United States Patent [19]

Adams et al.

[11] Patent Number: 5,199,054

[45] Date of Patent: Mar. 30, 1993

[54] METHOD AND APPARATUS FOR HIGH RESOLUTION INSPECTION OF ELECTRONIC ITEMS

[75] Inventors: John A. Adams, Escondido; Bruce D. Baker, Olivenhain; Kerry L. Brown, Temecula; Robert L. Corey; Brian L. Ganz, both of San Diego; David C. Reynolds, San Marcos; Edward W. Ross, Escondido; Gerald S. Russell; Christopher S. Sexton, both of San Diego, all of Calif.

[73] Assignee: Four Pi Systems Corporation, San Diego, Calif.

[21] Appl. No.: 575,550

[22] Filed: Aug. 30, 1990

[51] Int. Cl.$^5$ .............................................. H01J 35/08
[52] U.S. Cl. ...................................... 378/21; 378/22; 378/138; 378/143; 378/145; 378/124
[58] Field of Search .................. 378/19, 21, 22, 138, 378/205, 10, 62, 143, 144, 145, 119, 124, 123; 250/310, 307

[56] References Cited

U.S. PATENT DOCUMENTS

| 2,677,585 | 1/1954  | Gradstein      | 378/99  |
|-----------|---------|----------------|---------|
| 2,998,518 | 8/1961  | Guntert        | 378/99  |
| 3,091,692 | 5/1963  | Verse          | 378/20  |
| 3,812,288 | 5/1974  | Walsh et al.   | 358/111 |
| 4,075,489 | 2/1978  | Neal et al.    | 378/10  |
| 4,139,776 | 2/1979  | Hellstrom      | 204/118 |
| 4,160,909 | 7/1979  | Froggatt       | 378/12  |
| 4,340,816 | 7/1982  | Schott         | 378/22  |
| 4,352,021 | 9/1982  | Boyd et al.    | 378/12  |
| 4,516,252 | 5/1985  | Linde et al.   | 378/23  |
| 4,521,902 | 6/1985  | Peugeot        | 378/137 |
| 4,675,892 | 6/1987  | Plessis et al. | 378/145 |
| 4,688,241 | 8/1987  | Peugeot        | 378/137 |
| 4,720,633 | 1/1988  | Nelson         | 250/310 |
| 4,724,320 | 2/1988  | Ino et al.     | 250/310 |
| 4,730,350 | 3/1988  | Albert         | 378/99  |
| 4,809,308 | 2/1989  | Adams et al.   | 378/99  |
| 4,852,131 | 7/1989  | Armistead      | 378/4   |
| 4,926,452 | 5/1990  | Baker et al.   | 578/58  |
| 4,977,328 | 12/1990 | Van Vucht      | 250/307 |
| 5,020,086 | 5/1991  | Peugeot        | 378/137 |
| 5,102,498 | 4/1991  | Cuzin et al.   | 378/4   |

FOREIGN PATENT DOCUMENTS

| 0225969 | 6/1987  | European Pat. Off. .   |
| 1138617 | 10/1979 | Fed. Rep. of Germany . |
| 2946443 | 5/1981  | Fed. Rep. of Germany . |
| 812792  | 5/1937  | France .               |
| 868830  | 5/1961  | United Kingdom .       |

OTHER PUBLICATIONS

Hasenkamp, "Radiographic Laminography", *Materials Evaluation*, Aug. 1974, pp. 169–180.
Moler, "Development of a Continuous Scanning Laminograph", Final Report No. IITRI V6034-24, Oct., 1968.

(List continued on next page.)

*Primary Examiner*—Constantine Hannaher
*Assistant Examiner*—Don Wong
*Attorney, Agent, or Firm*—Dennis H. Epperson

[57] ABSTRACT

A high resolution laminography system for the inspection of integrated circuits wherein a beam of highly focused electrons is traced in a circular pattern on a flat target within a vacuum chamber. The target converts the electron beam into X-rays, so that a source of X-rays is produced which rotates in synchronization with a rotating detector assembly. An object is placed within the vacuum chamber, between the X-ray source and the detector so that an X-ray cross sectional image of a cutting plane of the object is produced. A computer and feedback system controls image acquisition and an automated positioning system. The computer system can also operate under program control to automatically analyze data, measure characteristics of the object under inspection, and make decisions regarding the acceptability of the object's quality. The invention also employs a channeltron imager to directly image the target so that the condition of the target may be monitored, and electron drift within the system can be compensated for.

14 Claims, 23 Drawing Sheets

OTHER PUBLICATIONS

Blanche, "Nondestructive Testing Techniques for Multilayer Printed Wiring Boards", Nondestructive Testing: Trends and Technique, NASA SP-5082, Oct. 1986, pp. 1-13.

Hamre, "Nondestructive Testing Techniques for Multilayer Printed Wiring Boards", Report No. IITRI-E60-24-15, Sep. 1965.

Soron, IRT Corp., "X-Ray Inspection Meets Increased PWB Througput", Density Challenge-Part 1, *Electronics*, Oct. 1987, pp. 36-37.

Pound, "Image Processing Boosts the Power of Non-destructive Testing", *Electronic Packaging and Production*, Jun. 1985.

Casey, "X-Ray Inspection", *Manufacturing Systems*, Jul. 1987, p. 18ff.

Phelps, Christi, "Four Pi Captures Contract, Capital; Unveils Product", *San Diego Business Journal*, Week of Oct. 10-16, 1988.

Smith et al., "Fast Circular Tomography Device for Cardiac Imaging: Image Deflection Mechanism and Evaluation", *IEEE Transactions on Medical Imaging*, vol. MI-6, No. 2, Jun., 1977, pp. 169-173.

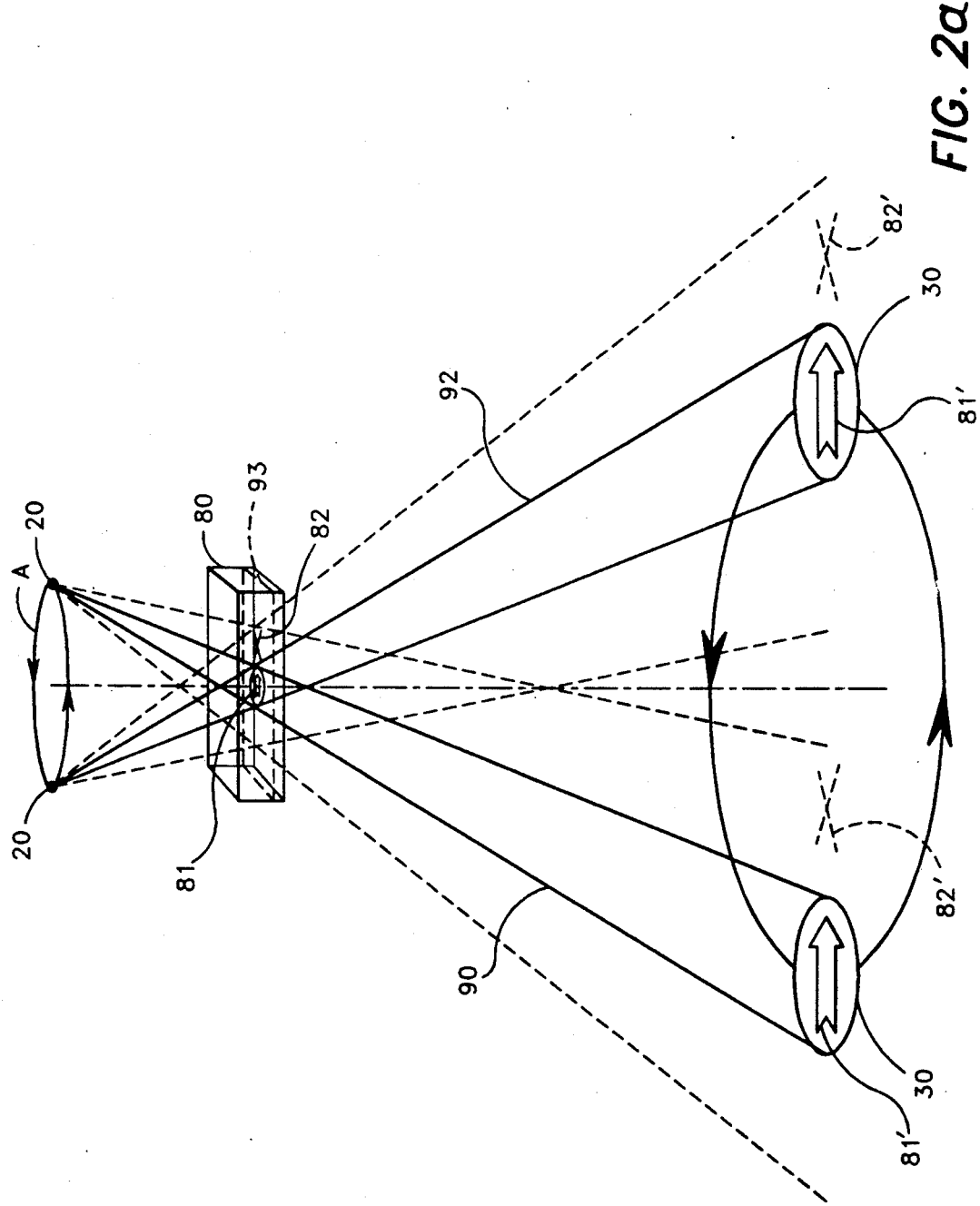

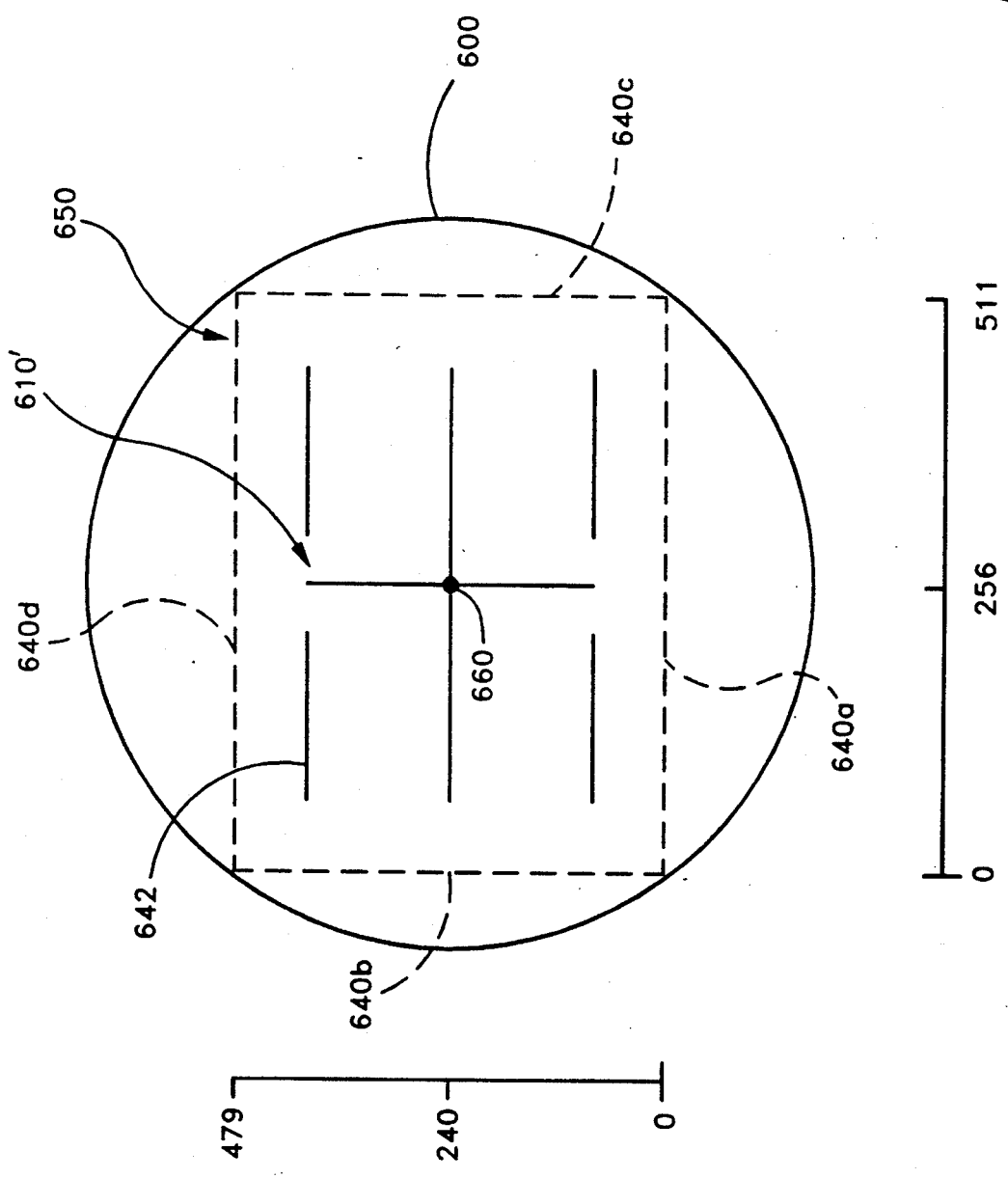

METHOD AND APPARATUS FOR HIGH RESOLUTION INSPECTION OF ELECTRONIC ITEMS

FIELD OF THE INVENTION

The present invention relates to automated inspection of electronic devices, in particular to automated inspection of electrical interconnections formed on integrated circuits and the like.

BACKGROUND OF THE INVENTION

Recent advances in circuit manufacturing technology have spawned increases in circuit complexity while simultaneously allowing for production of smaller and smaller circuits. For example, with the advances in "bump" or "flip chip" technology, electrical interconnections, which had previously been on the order of 0.020 inches between centers, are approaching 0.001 inch (25 microns) between centers. In addition, as the manufacture of circuit boards becomes ever more complex due to increasing lead count, decreasing lead pitch, and the switch to double-sided construction, it is important that the manufacturing engineer obtain real-time data about the circuit manufacturing process.

Presently, the best circuit board production lines produce assemblies with a solder joint defect rate of about 10-50 parts-per-million (PPM). Thus, as the number of solder connections on a circuit board increases, it becomes increasingly important to reduce joint solder-defect levels through process control feedback, and circuit board inspection. For example, for a circuit board design having 100,000 solder connections, and a joint defect level of 10 PPM, less than 40% of the circuit boards produced will be defect free.

The trend in manufacturing is toward more joints per board. There are boards being designed with over 150,000 connections on a single small board. In addition, advanced techniques are being used to increase the complexity of interconnections on integrated circuit (IC) chips as well. Therefore, additional means must be employed to further reduce the process defect level. Even with further process improvements, statistical process control, and closed loop feed-back, many products will still require an inspection system to reduce the remaining defect levels to acceptable rates for product shipment.

It has become apparent that, with increased circuit complexity and decreased circuit size, visual inspection by subjective human inspectors has become inadequate. Consequently, the circuit manufacturing industry has sought to develop an automated circuit inspection system which is capable of meeting the needs of present circuit board manufacturers. Inspection systems in the past have met with limited success for through hole technology boards and single-sided surface mount technology (SMT) boards. The most successful of these has been automated transmission X-ray. For example, U.S. Pat. No. 4,809,308 by Adams, et al., discloses an automated transmission X-ray device for performing circuit board solder quality inspections. It has been found, however, that automated transmission X-ray exhibits additional problems with double-sided SMT boards due to the overlapping interference of the images produced by the top side components with the images produced by components on the bottom side of the circuit board. That is, when an X-ray beam penetrates through two separate connections on both sides of a circuit board, the image formed on a detector is a composite image of both connections. This could present serious problems when attempting to analyze each connection individually. Because of the shortcomings exhibited by past automated inspection systems, a new automated circuit inspection technology was needed.

Recent developments in scanned-beam laminography (SBL) have provided improved resolution and accuracy in the inspection of electronic devices, particularly for high component density and double-sided circuit boards. By laminographically scanning an electrical connection, a cross-sectional image of the electrical connection can be produced which significantly reduces the overlapping image interference exhibited in transmission X-ray inspection systems. The introduction of SBL for the automated inspection of circuit boards has provided a means for analyzing individual connections on high density and double-sided circuit boards. Automated SBL typically provides for increased image resolution without requiring the complex mechanical operations that are typical of many automated inspection systems. Thus, automated SBL has proven to be superior for inspection of high density circuitry, and for applications which require the inspection of multiple layers within an object. Such an automated laminographic inspection system which produces cross-sectional images of electrical connections on a circuit board is described in U.S. Pat. No. 4,926,452, issued May 15, 1990.

Until now, SBL automated circuit inspection systems have been suitable for uses such as the inspection of solder connections on circuit boards. However, with the advent of integrated circuit designs wherein the entire circuitry that would normally be placed on a circuit board is instead deposited onto a silicon substrate, higher resolution inspection systems than had been previously contemplated have become a priority. With chip-level connections in the sub-micron range (i.e., 1.0 microns and smaller), the current technique of circuit inspection is not very practical. Thus, a need exists for a high-resolution, automated circuit inspection system which is capable of inspecting interconnections and circuitry (e.g., within an integrated circuit) using a resolution sufficient to analyze connections in the sub-micron range.

SUMMARY OF THE INVENTION

The present invention is directed to an apparatus and a method for the inspection of micro-features of electrical components such as an integrated circuit chip. The invention produces high resolution cross-sectional images of the micro-features which are then analyzed by an image analysis computer system. The cross-sectional images of the inspected micro-features are analyzed to locate defects, and, if defects are found, to determine the type of defects.

In particular, the present invention is a high resolution laminography system which comprises a source of electrons which generates an electron beam, a deflector for steering the electron beam, and a target wherein electromagnetic energy is emitted from the target when the electron beam impinges upon the target, which includes an imagable feature. The high resolution laminography system further comprises a laminographic detector for producing a laminograph of an object illuminated by the electromagnetic energy emitted by the target, and an SEM detector for producing an SEM micrograph of the target imagable feature in response to illumination of the feature by the electron beam.

In one embodiment, the system as defined in Claim 1 further comprises an image analysis system for analyzing characteristics of the SEM micrograph image of the feature, and providing an output signal in response to the analysis, and a feedback system which receives the output signal from the image analysis system, processes the output signal and provides a control signal to the electron beam deflector. In a particularly preferred embodiment, the feedback system comprises a digital Look-Up-Table.

In a further embodiment, the imagable feature on the target comprises four points, wherein two of the points lie on a line which is perpendicular to a line defined by two others of the points.

In another embodiment, the target comprises a plurality of concentric rings, or in an alternative embodiment, the target has a cylindrical interior surface.

In a further embodiment, the SEM detector comprises a channeltron imager. The present invention may also include an electron collector for preventing electrons from striking the object, and a piezoelectric translation stage for vertically positioning the object.

In still a further embodiment, the detector comprises a fluorescent screen, an optical derotation device and a camera. In a preferred form of this embodiment, the fluorescent screen comprises Gadolinium Oxysulfide.

The high resolution laminography system may also comprise a means for supporting an object within a vacuum chamber, a source of electromagnetic energy which illuminates the object, and a laminographic detector for producing a laminograph of the object when illuminated by the electromagnetic energy.

In one embodiment the detector is situated within the vacuum chamber, and is supported by magnetic bearings.

In a further embodiment, the laminography system of the present invention comprises a pair of differential vacuum pumps.

The method of producing high resolution laminographs in accordance with the present invention comprises the steps of generating an electron beam, steering the electron beam with a deflector, striking a target with the electron beam, wherein electromagnetic energy is emitted from the target when the electron beam impinges upon the target, the target having an imagable feature, producing a laminograph of an object illuminated by the electromagnetic energy using a laminographic detector, and producing an SEM micrograph of the target imagable feature in response to illumination of the feature by the electron beam.

The method of producing high resolution laminographs may also comprise the steps of analyzing characteristics of the SEM micrograph image of the feature, and providing an output signal in response to the analysis, and providing a feedback system which receives the output signal from the image analysis system, processes the output signal and provides a control signal to the electron beam deflector.

In a further embodiment, the analyzing step comprises the step of, determining the location of the feature image within the micrograph, calculating the distance between the determined location of the feature image and the center of the micrograph, and producing a voltage signal as a function of the calculated distance appropriate to cause the feature image to be centered within the micrograph.

The method of producing high resolution laminographs in accordance with the present invention may also comprise the steps of supporting an object within a vacuum chamber, illuminating the object using a source of electromagnetic energy, and producing a laminograph of the object illuminated by the electromagnetic energy using a laminographic detector. In one embodiment, the method may also comprise the step of situating the detector within the vacuum chamber.

BRIEF DESCRIPTION OF THE DRAWINGS

FIGS. 2a and 2b are simplified schematic diagrams which depict the laminographic geometry used in the present invention, and illustrate the effect of shifting the relative location of the path traced by the X-ray source.

FIG. 9 shows an X-ray image of an exemplary fiducial trace pattern within an integrated circuit.

DETAILED DESCRIPTION OF THE INVENTION

As used throughout, the term "radiation" refers to electromagnetic radiation, including but not limited to the X-ray, gamma and ultraviolet portions of the electromagnetic radiation spectrum.

Figure 1:
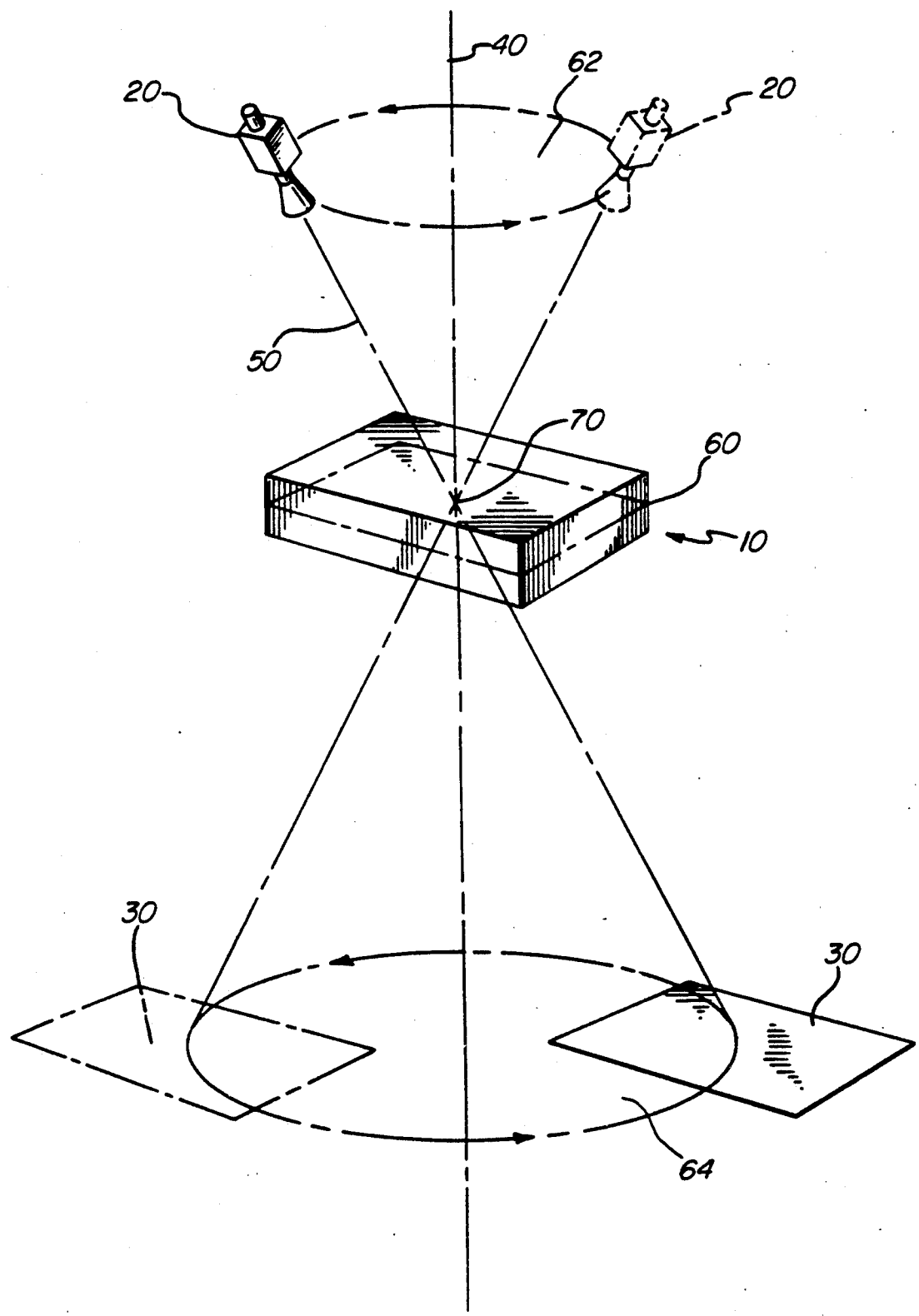
FIG. 1 is a simplified schematic diagram which shows the main components of a laminographic system and their approximate geometric relationship to one another.

FIG. 1 shows a schematic representation of the laminographic geometry used in the present invention. An object 10 under examination, for example, an integrated circuit, is held in a stationary position with respect to a source of X-rays 20 and an X-ray detector 30. Synchronous rotation of the X-ray source 20 and detector 30 about an axis 40 causes an X-ray image of a plane 60 within the object 10 to be formed on the detector 30. In the embodiment shown in FIG. 1, the axis 40 is the common axis of rotation for both the X-ray source 20 and the detector 30, however, it should be noted that the rotation of the X-ray source 20 need not occur about the same axis as the rotation of the detector 30. In practice it is sufficient that the planes 62 and 64, defined by the rotation of the source 20 and detector 30 respectively, are parallel to one another.

The image plane 60 is substantially parallel to the planes 62 and 64. As the X-ray source 20 and the detector 30 rotate in synchronization, a family of cones is defined around the circular path traced by the source 20 and the detector 30. Each cone has an apex defined by the X-ray source 20, and a base defined by the circular detector 30. The set of points defined by the intersection of the entire family of cones around a complete rotation of the source and detector constitutes the imaged region, or field of view, of the focal plane 60. Thus, an in-focus, cross-sectional X-ray image of the portion of the object 10 within the field of view at the imaged region of the focal plane 60 is formed on the detector 30 as the source and detector synchronously rotate about an intersection point 70. Structures within the object 10 which lie outside of plane 60 form a blurred X-ray image on the detector 30.

Figure 2B:
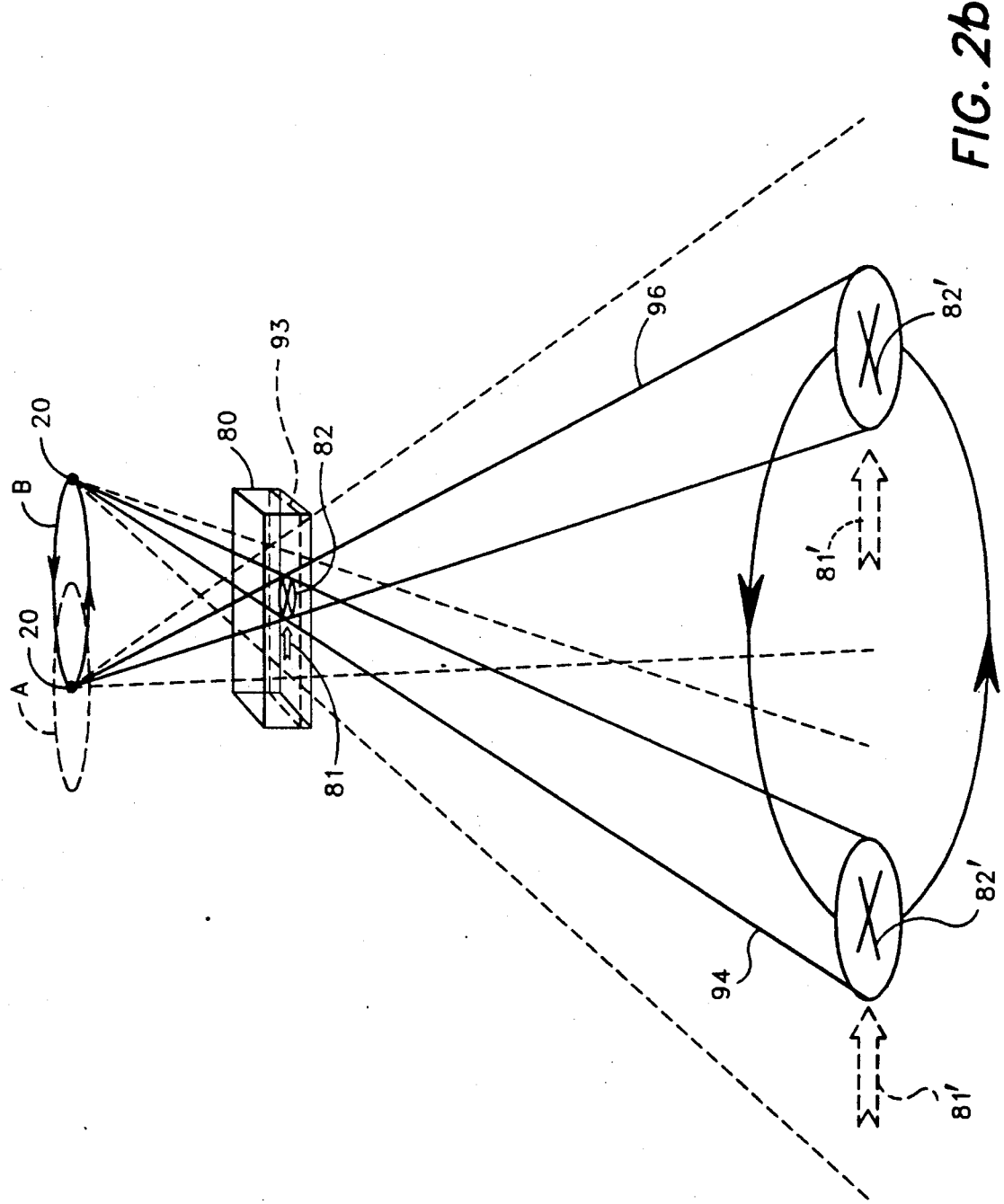

FIGS. 2a and 2b depict source and detector configurations that image different regions, i.e., fields of view, within the same focal plane of an object 80. In FIG. 2a, the source 20 is shown to rotate about a center point in a circular path, A. In FIG. 2b, the source 20 is shown to rotate in a second circular path, B, about another center point which is linearly shifted from the center point of the path A. The object 80 shown in FIGS. 2a and 2b has test patterns in the shape of an arrow 81, and a cross 82 embedded within the object 80. In FIG. 2a, cones 90 and 92, defined by the X-ray source 20 and detector 30 at two different locations along their path of rotation, are shown to intersect in an image plane 93 at substantially the same location as the arrow 81, so that as the source and detector rotate in synchronization, an image of the arrow 81 is reinforced on the detector 30. Thus, the configuration shown in FIG. 2a produces a cross-sectional image of the arrow 81 on the detector 30. In FIG. 2b, a different circular path that is horizontally displaced from the path traced in FIG. 2a is followed by the X-ray source 20. In this case, cones 94 and 96, defined by the X-ray source 20 and detector 30 at two different locations along their path of rotation, are shown to intersect in an image plane 97 at substantially the same location as the cross 82. Thus, as the source and detector rotate in synchronization, an image of the cross 82 is reinforced on the detector 30, so that the configuration shown in FIG. 2a produces a cross-sectional image of the cross 82 on the detector 30.

Figure 3A:
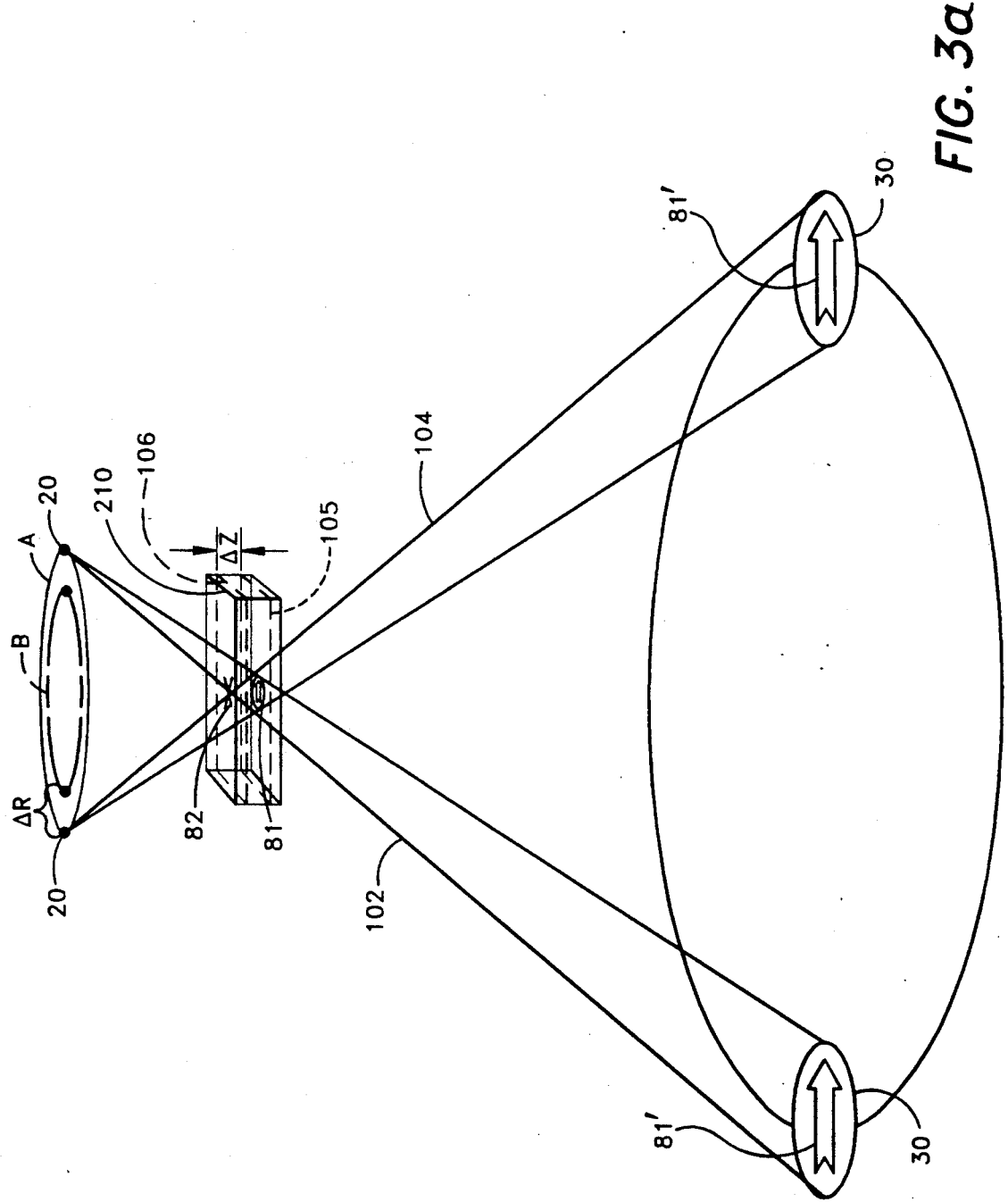
FIGS. 3a and 3b are simplified schematic diagrams which depict the laminographic geometry used in the present invention, and illustrate the effect of varying the radius of the path traced by the X-ray source.
Figure 3B:
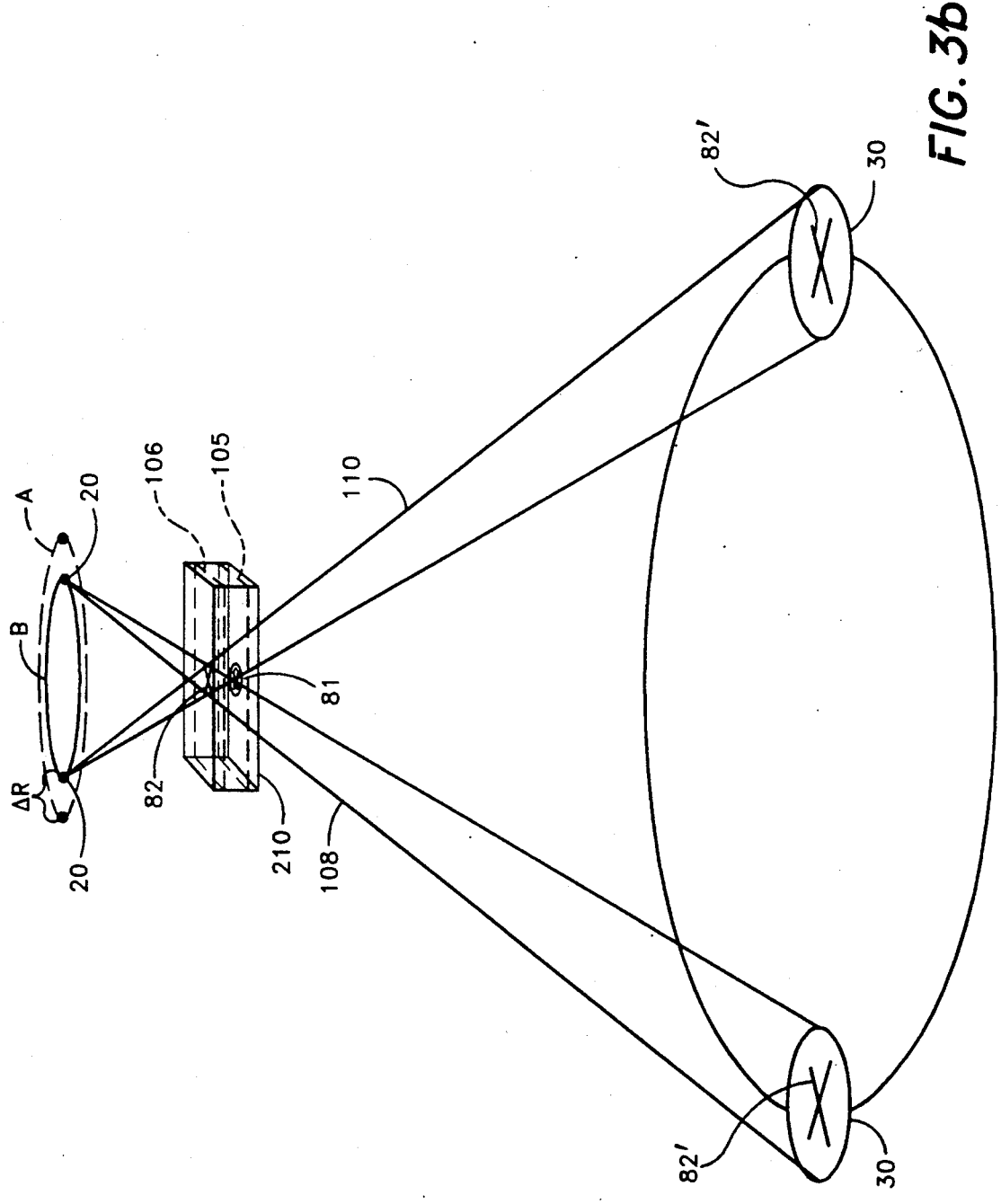

FIGS. 3a and 3b depict source and detector configurations that image regions within different planes of an object 100. The object 100 also has test patterns in the shape of the arrow 81, and the cross 82 embedded within the object 100. In FIG. 3a, cones 102 and 104, defined by the X-ray source 20 and detector 30 at two different locations along their path of rotation, are shown to intersect in an image plane 105 at substantially the same location as the arrow 81, so that as the source and detector rotate in synchronization, an image of the arrow 81 is reinforced on the detector 30 to produce a cross-sectional image of the arrow 81 on the detector 30. In FIG. 3b, a different circular path, having a smaller radius than the path shown in FIG. 3a, is followed by the X-ray source 20. Thus, cones 108 and 110, defined by the X-ray source 20 and detector 30 at two different locations along their path of rotation, are shown to intersect in an image plane 106 at substantially the same location as the cross 82, so that the configuration shown in FIG. 2a produces a cross-sectional image of the cross 82 on the detector 30.

Thus, FIGS. 2a, 2b, 3a and 3b illustrate how different regions of a specimen under inspection can be imaged onto the detector 30 by manipulating the path traced by the X-ray source 20. For example, this may be done by electrostatically deflecting an electron beam which produces X-rays when it strikes various locations on a target. By deflecting an electron beam, electrons may be caused to strike different regions of the target in a desired pattern, thereby causing the X-ray source 20 to trace a desired path on the target.

FIGS. 4a-4e show laminographs produced by the above described laminographic technique. The object 10 shown in FIG. 4a has test patterns in the shape of the arrow 81, the cross 82, and a circle 83 embedded within the object 10 in three different planes 60a, 60b and 60c, respectively.

Figure 4A:
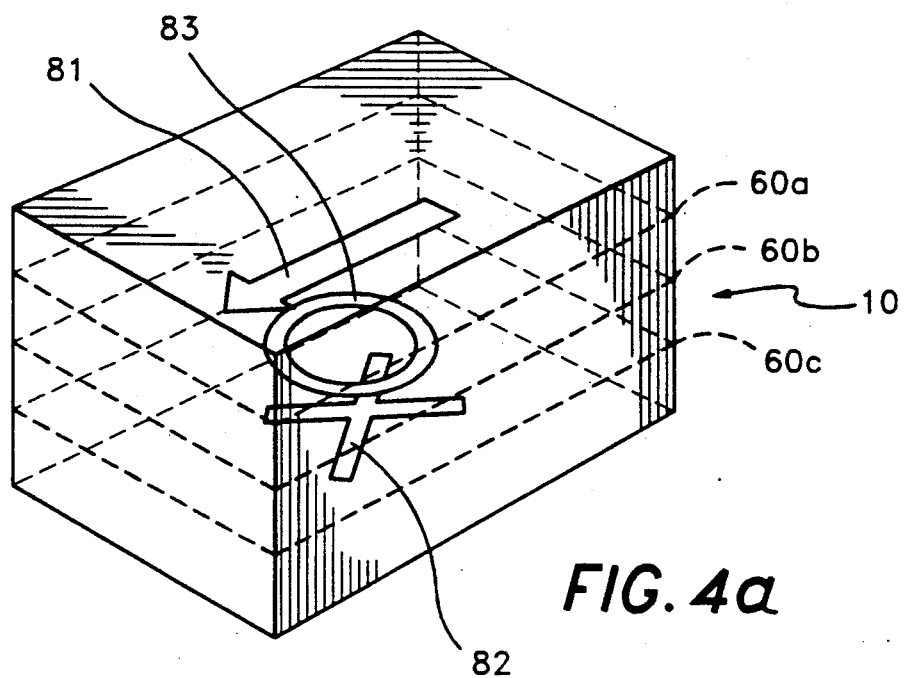
FIGS. 4a-4e illustrate the manner in which images of features in different planes within an object can be imaged using a laminography system.
Figure 4B:
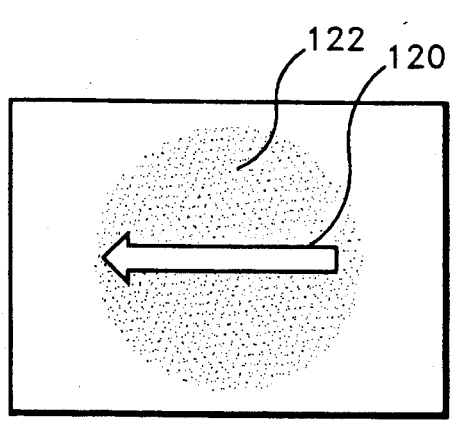

FIG. 4b shows a typical laminograph of object 10 formed on detector 30 when the point of intersection 70 lies in plane 60a of FIG. 4a. The image 120 of arrow 81 is in sharp focus, while the images of other features within the object 10, such as the circle 83 and cross 82 form a blurred region 122 which does not greatly obscure the arrow image 120.

Figure 4C:
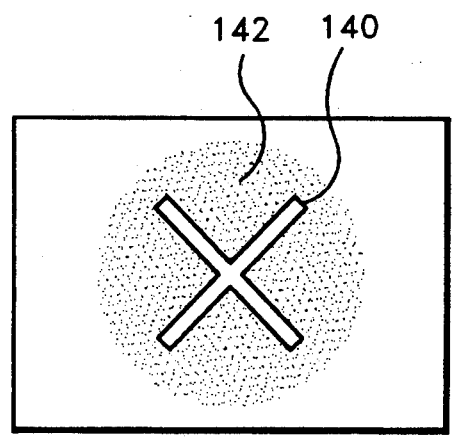
Figure 4D:
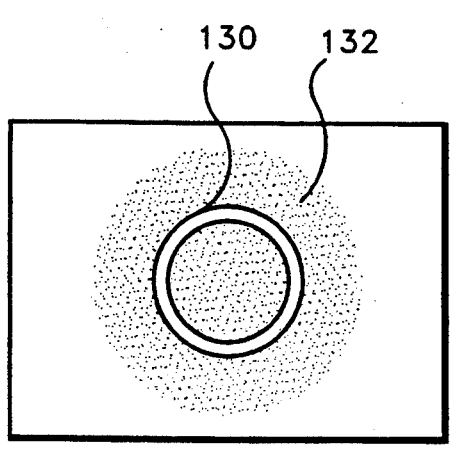

Similarly, when the point of intersection 70 lies in plane 60b, the image 130 of the circle 83 is in sharp focus as seen in FIG. 4d. The arrow 81 and cross 82 form a blurred region 132.

FIG. 4c shows a sharp image 140 formed of the cross 82 when the point of intersection 70 lies in plane 60c. The arrow 81 and circle 83 form blurred region 142.

Figure 4E:
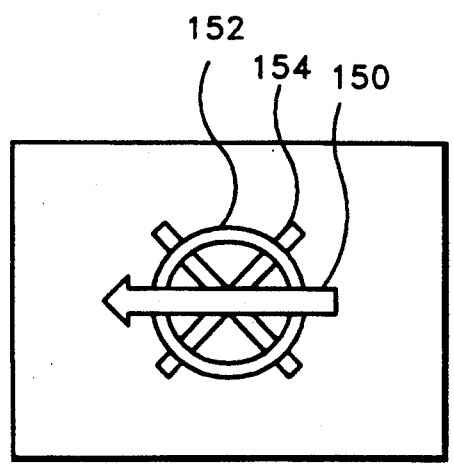

For comparison, FIG. 4e shows an X-ray shadow image of object 10 formed by conventional projection radiography techniques. This technique produces sharp images 150, 152 and 154 of the arrow 81, circle 83 and cross 82, respectively, which overlap one another. FIG. 4e vividly illustrates how multiple characteristics contained within the object 10 may create multiple overshadowing features in the X-ray image which obscure individual features of the image.

Figure 5:
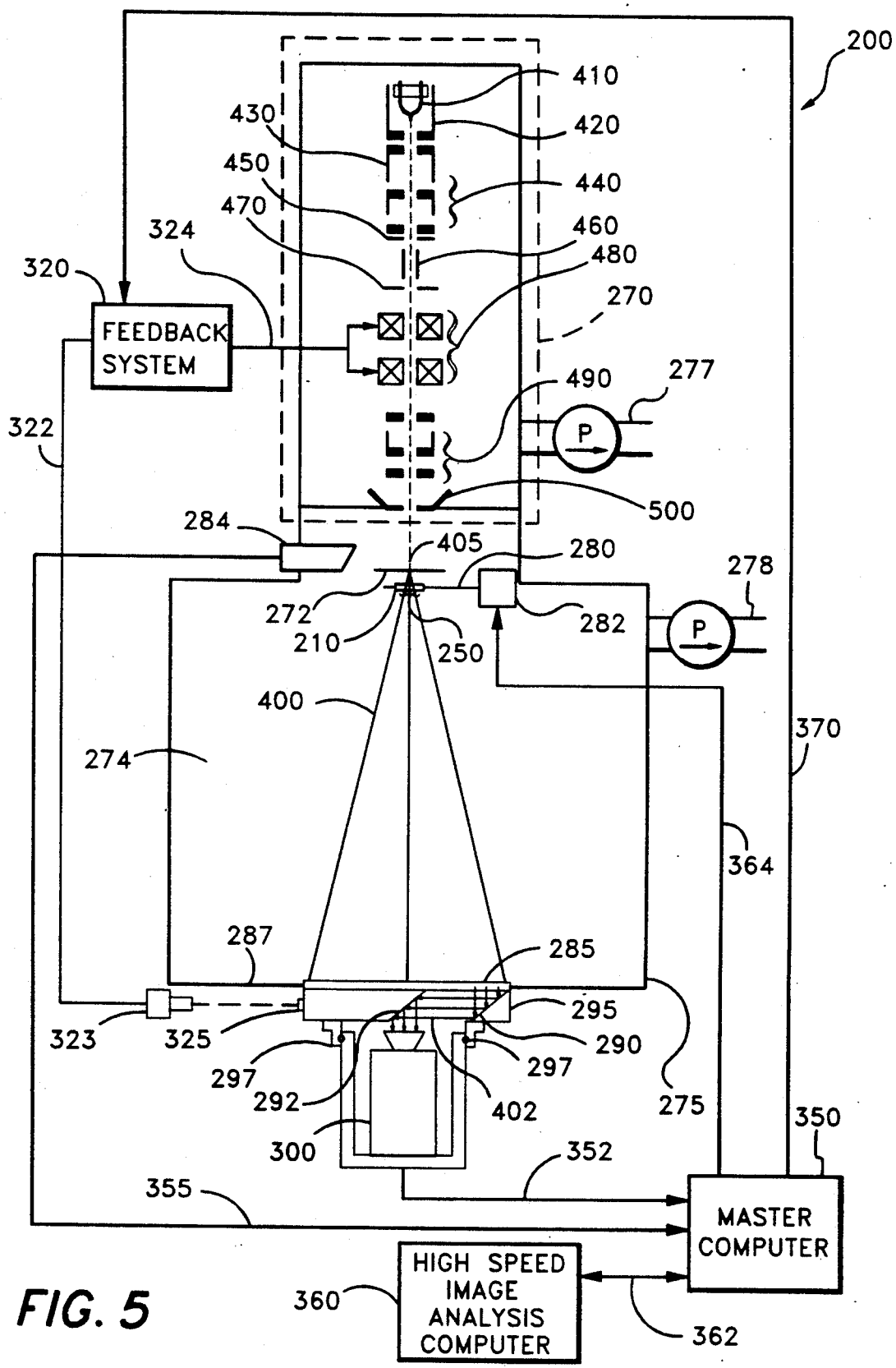
FIG. 5 is a simplified schematic diagram of the high resolution laminography system of the present invention.
Figure 6A:
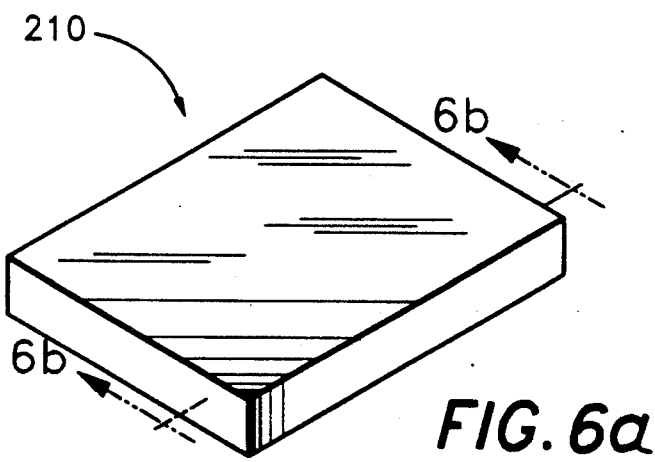
FIG. 6a is a perspective view showing the general visual appearance of a typical integrated circuit chip.
Figure 6B:
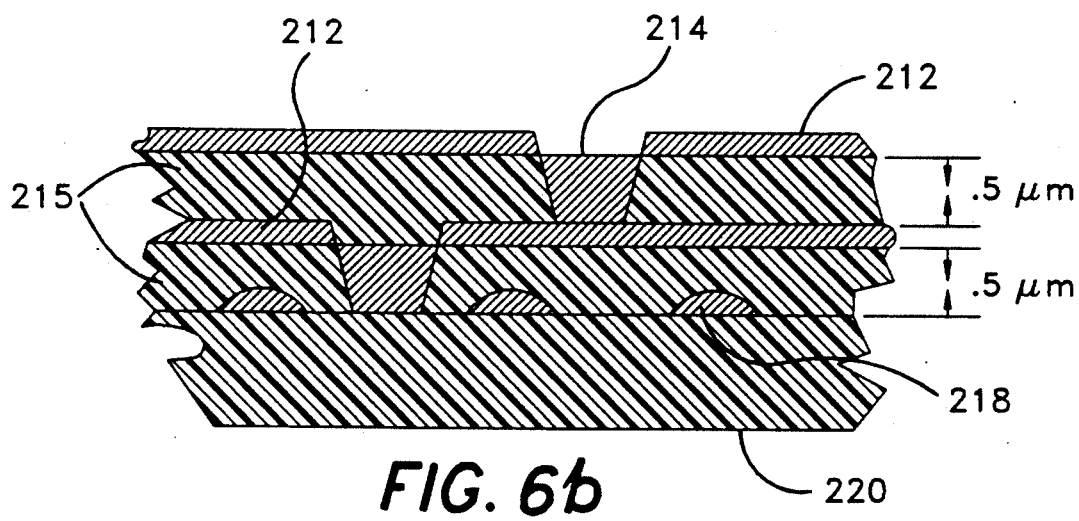
FIG. 6b is a side cross-sectional view showing the different trace layers within an integrated circuit.
Figure 6C:
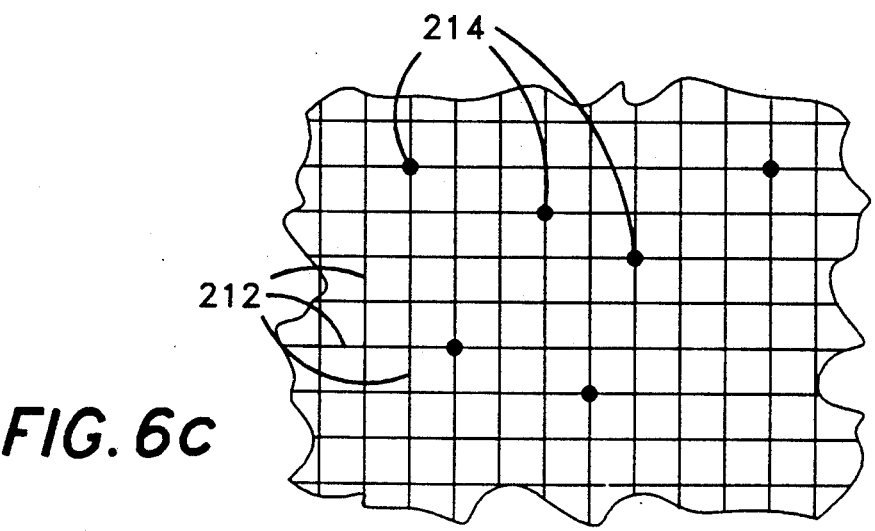
FIG. 6c is a plan view which shows the traces and electrical interconnections typically found within the different layers of an integrated circuit.

FIG. 5 illustrates a schematic diagram of one embodiment of the high resolution laminography system 200 of the present invention. In this embodiment, the object under inspection is an integrated circuit 210 having multiple conductive traces, and multiple electrical interconnections formed therein. FIG. 6a illustrates the general visual appearance of a die used to make the integrated circuit 210 which is exemplary of an integrated circuit die that may be inspected using the apparatus of the present invention. The integrated circuit 210 is typically one of multiple integrated circuits formed from a silicon wafer. The present invention may also be used to inspect integrated circuit wafers. The integrated circuit 210 may, for example, be electrically connected to a circuit board, or a similar supporting structure. The dimensions of the integrated circuit 210 are typically on the order of 0.25"×0.25", although smaller or larger integrated circuit chips may also comprise the integrated circuit 210. FIG. 6b, which is an exemplary side cross-sectional view of the integrated circuit 210, shows how multiple layers of conductive trace paths 212 are separated by insulating layers 215. The insulating layers 215 are typically on the order of 0.5 micrometers thick, and are generally made of plastic or resin. The traces 212 are electrically connected at selected locations by electrical interconnections 214 which may be made of copper or other electrically conductive material. The traces 212, as well as the electrical interconnections 214 can be used to form conductive paths between circuit elements, which are formed within a silicon substrate 220, at junctions 218 at the surface of the silicon substrate. FIG. 6c, which is a top view enlargement of a region 250 of the integrated circuit 210, clearly shows the conductive traces 212 and the electrical interconnections 214. Typically, both the conductive traces 212 and the electrical interconnections 214 are formed of metal. The metal traces are generally etched in a grid pattern in different layers on the surface of the substrate 220.

The device of the invention acquires cross-sectional images of the electrical interconnections 214 and traces 212 using the previously described laminographic method or other methods capable of producing equivalent cross-sectional images. The cross-sectional images of the traces 212 and the electrical interconnections 214 are automatically, or visually, evaluated to determine their quality. Based on the evaluation, a report of the electrical interconnection quality is presented to the user.

The invention, as shown in FIG. 5, comprises an electron focusing column 270 which is positioned adjacent a tungsten target 272 and the integrated circuit 210 within a specimen chamber 274 of a vacuum chamber 275. The integrated circuit 210 is supported by a fixture 280. The fixture 280 is attached to a piezoelectric "inchworm" translation stage 282 which is capable of moving the fixture 280 and integrated circuit 210 along the Z axis (i.e., vertically) in increments of approximately one micron. A channeltron electron imager 284 is positioned near the target 272 so as to image the target directly, thereby forming a micrograph of the target, much as is done in a scanning electron-beam microscope (SEM). Separate pumps 277 and 278 are employed to maintain the vacuum within the electron focusing column 270 and the specimen chamber 274 respectively. In one embodiment, the air pressure within the electron focusing column is maintained at $10^{-9}$ Torr, and the pressure within the specimen chamber is maintained at approximately $10^{-7}$ Torr. A fluorescent screen 285 is deposited onto a window 287 which seals the vacuum chamber 275. A rotating X-ray detector assembly, such as that described in U.S. Pat. No. 4,926,452, comprises a first rotating mirror 290, and a second rotating mirror 292, and is positioned adjacent the fluorescent screen 285 outside of the vacuum tube 275 opposite the electron focusing column 270. The rotating mirrors 290, 292 are affixed to a turntable 295 which, in turn, is supported by bearings 297. A camera 300 is positioned opposite mirror 292 for viewing images reflected into the mirrors 290, 292 from the fluorescent screen 285. A feedback system 320 has an input connection 322 from a sensor 323 which detects the angular position of the turntable 295 (and thereby the mirrors 290, 292). The feedback system 320 also has an output connection 324 to X and Y deflection coils 480 within the electron focusing column 270. A position encoder 325 is attached to turntable 295. The position sensor 323 is mounted adjacent encoder 325 in a fixed position. The camera 300 is connected to a master computer 350 via an input line 352. The master computer 350 also receives input from the channeltron 284 via an input line 355. The master computer 350 is connected to a high speed image analysis computer 360. Data is transferred between the master computer 350 and the image analysis computer 360 via data bus 362. An output line 364 from master computer 350 connects the master computer to the piezoelectric translation stage 282. A line 370 connects the master computer 350 to the feedback system 320, which controls the X and Y deflection octupole coils 480.

In addition to the elements described above, a support table that provides a rigid, vibration free platform for structurally integrating the major functional elements of the invention is provided. For applications involving the high resolution laminography system of the present invention, it is especially important to minimize vibrations caused by external as well as internal sources. Thus, the support table is advantageously placed on isolation supports to prevent the transmission of vibrations from the ground or other external sources. It is also advantageous to magnetically isolate the apparatus of the present invention to prevent magnetic interference from outside sources (e.g., the magnetic field produced by the earth). A load/unload port for inserting and removing the specimen (e.g., the integrated circuit 210) and an operator station for interfacing with the master computer 350 are also incorporated within the present invention.

In operation of the laminography system 200, high-resolution, cross-sectional X-ray images of the electrical interconnections 214 and traces 212 within the integrated circuit 210 are obtained using the laminographic method described above in reference to FIGS. 1-5. Specifically, the electron focusing column 270 focuses a rotating electron beam spot onto the target 272 which in turn produces a rotating source of X-rays 400 originating within the target 272. The X-rays 400 illuminate the region 250 of the integrated circuit 210, which includes the traces 212 and the electrical interconnections 214 within the region 250. The X-rays 400 which penetrate the integrated circuit 210, and are incident on the fluorescent screen 285, produce visible light 402 whose intensity is directly related to the energy of the X-rays 400 incident on the detector screen 285. The visible light 402 that is intercepted by the rotating mirror 290 is reflected to the rotating mirror 292, and is reflected therefrom into the lens of the camera 300. Note that only that light which is intercepted by the mirror 290 will be detected by the camera 300, so that the mirror 290 acts as a rotating detector.

Dynamic alignment of the position and path of the X-ray source on the target 272, produced by the electrons focused on the target 272, with the position of rotating mirror 290 is precisely controlled by feedback system 320. The feedback system 320 correlates the position of the rotating mirror 290 with calibrated X and Y deflection values stored in a look-up table (LUT). Drive signals proportional to the calibrated X and Y deflection values are transmitted to the X-Y deflection octupole coils 480 within the electron focusing column 270. In response to these drive signals, the octupole coils 480 deflect an electron beam 405 to locations on the target 272 such that the position of the X-ray source spot rotates in synchronization with the rotation of the mirror 290 in the manner previously discussed in connection with FIG. 1.

Thus, the X-rays 400 which penetrate the integrated circuit 210 and strike fluorescent screen 285 create a visible image of a single plane within the region 250 of the integrated circuit 210. The camera 300 typically comprises a low light level closed circuit TV (CCTV) camera which transmits electronic video signals corresponding to the X-ray and visible images to the master computer 350 via line 352. The electronic video format image is transferred to the high speed image analysis computer 360 via line 362. The image analysis computer 360 analyzes and interprets the image to determine the quality of the traces 212 and the electrical interconnections 214. It should be noted that it is not always necessary to convert the X-rays 400 into optical signals using the phosphor detector 285. For example, a CCD camera, or a PLUMBICON type imaging device could be used to directly image the X-rays 400. In this embodiment, the CCD or PLUMBICON could be rotated on the turntable 295 instead of the mirrors 290, 292.

In addition, a variety of other detector schemes will be contemplated by one skilled in the art. For example, one skilled in the art will understand that it is possible to implement a detector scheme using a conventional Thompson tube. In such an embodiment, a Thompson tube having a Cesium Iodide screen could be mounted to the vacuum chamber 275 in the place of the fluorescent screen 285. The Cesium Iodide screen would convert incident X-rays into electrons, which could then be electrostatically focused and manipulated within the Thompson tube. The focused electrons then strike a scintillator so that a visible image is produced. The visible image may be derotated using an optical derotation assembly, or electronically derotated in response to appropriate signals provided to the deflection means within the Thompson tube. In another embodiment, the present invention may employ a fiber optic reducer to optically intensify the image produced on the fluorescent screen 285.

The master computer 350 also controls the Z-axis movement of piezoelectric translation stage 282, and thus the integrated circuit 210. Variations in the scan radius of the circular path traced by the X-ray source cause the location of the focal plane to move up or down in the Z direction. By varying the position of the integrated circuit 210 along the Z-axis using the piezoelectric translation stage 282, and concurrently varying the scan radius so that the focal plane corresponds to the position of the integrated circuit 210, different dimensions (and thereby magnifications) of the field of view region 250 can be obtained. In this manner, the laminography system 200 may zoom in or out of a given field of view. This zoom feature is particularly advantageous because it facilitates the location of different regions of interest on the integrated circuit 210.

The master computer 350 may also control the voltages applied to the X-Y deflection octupole coils 480 via the feedback system 320. As stated above, the electron beam 405 is typically deflected in a circular pattern so that, when the electrons strike a spot on the target 272, an X-ray source is produced on the target 272 originating proximate to the electron spot. By varying the voltages applied to the coils 480 to deflect the electron beam 405, the path traced by the X-ray source can be changed accordingly. For example, as will be discussed in greater detail below, finer slicing (e.g., in the sub-micron range) of the image planes along the Z-axis direction can be accomplished by slightly changing the radius of the circular path traced by the X-ray source. This is illustrated in FIGS. 3a and 3b. In addition, it is also possible to horizontally or vertically deflect the entire circular trace path in order to image different regions of the integrated circuit 210 within the same image plane (i.e., at the same level in the Z-axis direction). This is illustrated in FIG. 2a and 2b. Thus, large portions of the integrated circuit 210 can be inspected in a relatively short time, and vibrations are reduced, because mechanical positioning of the integrated circuit 210 is minimized.

ELECTRON FOCUSING COLUMN

The electron focusing column 270 is used to provide a steady beam of electrons 405 which strike a spot on the target 272. In order to provide maximum resolution for an image generated by a source of penetrating X-ray radiation, it is preferable that the X-rays 400 radiate from a point source of infinitesimal size. It is therefore advantageous to produce an electron spot on the target 272 that is minuscule, so that the X-ray source, produced proximate to the electron spot on the target 272, is as close to a point source as possible.

In one embodiment, the present invention employs a two lens electron focusing column such as that manufactured by FEI Company at 19500 N.W. Gibbs Drive, Suite 100, Beaverton, Ore. 97006-6907. The electron focusing column 270 advantageously provides up to 25 KeV of beam energy and a spot size of approximately 200-1000 Angstroms (0.02-0.1 microns). Typically, the electron beam energy will be from 1 KeV to 25 KeV to produce high resolution images of the integrated circuit 210 with maximum contrast. Note that the focusing column 270 is similar to those used in scanning electron microscopes for electron microscopy, so that a smaller spot size can be attained.

FIG. 5 illustrates the different components used to generate and focus the electron beam 405 within the focusing column 270. A source of electrons is provided by a Schottky cathode filament 410, which is the origin of the electron beam 405. A suppressor grid 420 allows for fine control of the emission current of the electron beam 405 by means of a voltage applied to the grid 420. The suppressor grid 420 also acts to suppress unwanted thermionic emission from the shank of the filament 410. Electrons are accelerated, or extracted, from the filament 410 by means of a voltage applied to an extractor 430. The voltage applied to the extractor 430 is approximately 5 kV in one embodiment. Once the electrons are extracted from the filament 410, the electron beam 405 is formed using a first focusing electrostatic lens 440.

Stray and scattered electrons are collected in a beam defining aperture 450 to further narrow the electron beam 405. The beam 405 then passes through blanking plates 460. It may, for example, be desirable to blank the electron beam 405 during mechanical alignment of the integrated circuit specimen 210. A voltage applied to the blanking plates 460 may be used to deflect the electron beam 405 into the blanking plates 460 so that the beam 405 does not strike the target 272. The beam 405 then passes through a blanking aperture 470 which may also be used to absorb electrons from the electron beam 405 after the beam 405 is deflected by the blanking plates 460. If the beam 405 is not blanked by means of the blanking plates 460 and the blanking aperture 470, the electron beam 405 passes through the octupole deflection coils 480. As stated above, the coils 480 are used to deflect the electron beam 405 in a desired pattern on the target 272. For example, the electron beam 405 may be deflected so that it follows a path which traces a circle of a desired radius and having a center at a desired horizontal and vertical displacement on the target 272. The voltage signals applied to the coils 480 advantageously comprise the outputs of the feedback system 320, as controlled by the master computer 350 and the sensor 323 which assures synchronization between the rotating detector mirror 290 and the rotating X-ray source on the target 272. Once the electron beam 405 has been deflected and synchronized by means of the coils 480, the beam 405 is focused again by a second focusing electrostatic lens 490 to form a sharper beam. The focusing lens 490 may also be used to dynamically focus the electron beam 405. That is, each time the electron beam 405 is deflected, the distance that the electrons travel (i.e., from the filament tip to the target surface) changes, so that there is a different focal length than before the deflection. In order to compensate for this, a small dynamic focusing voltage is applied at the focusing lens 490 so that the focal point of the electrons always occurs at the surface of the target. Finally, the focused beam 405 is accelerated through a pump aperture 500. The pump aperture helps to maintain a differential pressure between the vacuum within the electron focusing column 270, and the vacuum within the specimen chamber 274. The pump aperture 500 may also include a shutter (not shown) which closes each time a specimen is inserted into or removed from the specimen chamber 274 so as to maintain the fidelity of the vacuum within the focusing column 270. From the aperture 500, the electron beam 405 strikes the target 272 so that an electron spot is formed with a diameter from 200–1000 Angstroms. X-rays 400 are then emitted from the target 272, proximate to the electron spot.

The target 272 is advantageously constructed by depositing a thin layer of material onto a flat, thin substrate using conventional integrated circuit lithography techniques. The material forming the surface of the target 272 is selected so that the radiation produced when electron beam 405 strikes the surface of the target 272 has the desired energy characteristics. The radiation produced by bombarding a target material with an accelerated electron beam is known as Bremsstrahlung radiation. The characteristics of Bremsstrahlung radiation are determined primarily by the energy of the electron beam 405 and the material composition of the target 272 into which the electron beam is directed. In a preferred embodiment, the surface of the target 272 which is bombarded by electron beam 405 is covered with a layer of tungsten metal, and the substrate onto which the tungsten is deposited is beryllium.

The target 272 is sufficiently thin (e.g., on the order of 10 microns) to allow the location of the X-ray source to coincide substantially exactly with the location of the electron spot formed within the target 272. It is possible that some electrons will pass through the target 272, rather than being converted into X-rays. Therefore, an electron collection scheme could be provided in order to prevent the specimen (e.g., the integrated circuit 210) from being hit with electrons. In one embodiment, the specimen is given a negative voltage bias (on the order of a few volts) to deflect electrons which pass through the target 272. In another embodiment, a collection ring is positively biased and is positioned intermediate the target and the specimen, so that it attracts electrons which pass through the target 272. In still another embodiment, the target may be positively biased to decelerate the incident electrons.

It is also important that the target be substantially flat relative to the detecting screen 285. This is because the plane of rotation 62 of the X-ray source should be substantially parallel to the plane of rotation 64 of the detector 30, as shown in FIG. 1. In one embodiment, the tilt in the target 272 relative to the screen 285 should be less than 0.05 microns per 0.001 inch.

The electron focusing column 270 in conjunction with the flat target 272 thus provides a source of X-rays suitable for making high resolution X-ray images even when used in a geometry which magnifies the images. Additionally, the focusing column 270 has the capability of moving this source of X-rays in a circular pattern suitable for making laminographs. This circular motion is accomplished without sacrificing image resolution or speed of acquisition. Since the rotation of the radiation source is accomplished electronically, no moving parts are needed, thus eliminating vibrations and other undesirable characteristics of mechanical systems.

Figure 15B:
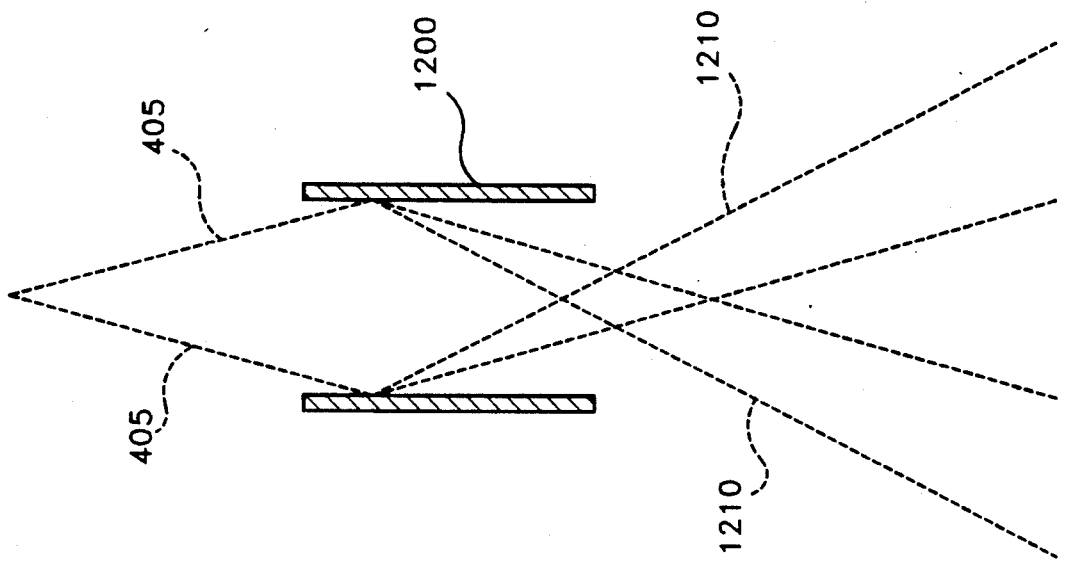
FIGS. 15a and 15b, shows a cross-sectional view of an alternative target formed as a hollow cylinder.
Figure 15A:
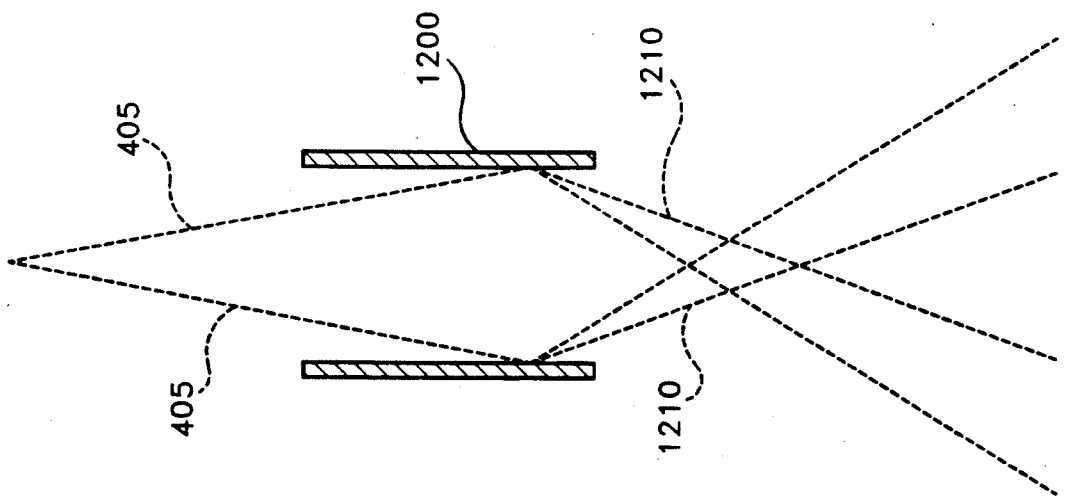
Figure 16:
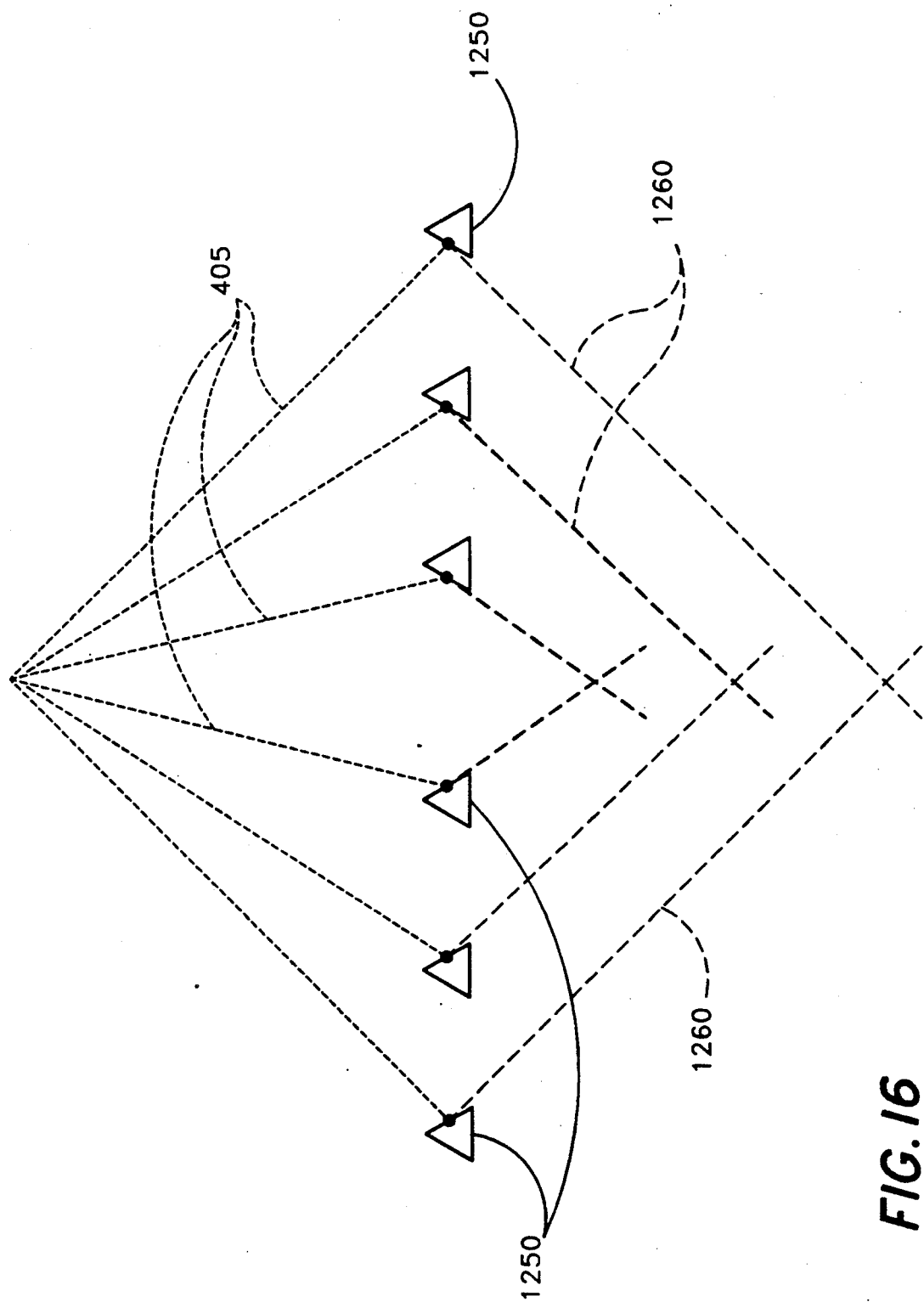
FIG. 16 shows a cross-sectional view of another embodiment of the target having concentric rings.

It will be understood that different configurations of the target 272 may be used in accordance with the present invention. For example, FIGS. 15a, 15b and 16 illustrate two possible embodiments of a target that may be used in accordance with the present invention. In FIGS. 15a and 15b, a cross-sectional view of an alternative target 1200 is shown. The target 1200 is constructed as a hollow cylinder which has a coating of tungsten, or similar material, on its inner surface. As shown in FIG. 15a, when the electron beam 405 is deflected in a circular pattern so that it strikes the interior surface of the target 1200, X-rays 1210, which are incident upon the detector, are emitted from the spots where the electron beam 405 strikes the target 1200 so that the X-rays intersect in the focal plane. When the path traced by the electron beam 405 is moved vertically up to another portion of the interior of the target 1200, as shown in FIG. 15b, the X-rays 1210 are emitted so that they intersect in another focal plane that is vertically displaced in the positive Z direction from the focal plane defined by the X-rays shown in FIG. 15a. Thus, distinct focal planes can be defined along the Z axis using the configuration of the target 1200 shown in FIGS. 15a and 15b.

FIG. 16 shows a cross-sectional view of another embodiment of the target. In the embodiment shown in FIG. 16, a target 1250 comprises multiple concentric rings which are formed so that X-rays 1260 are produced when the electron beam 405 is incident upon the surface of the target 1250. Each of the rings has a different radius so that objects in different focal planes along the Z axis are imaged when the electron beam 405 is deflected to trace a path on selected ones of the rings of the target 1250.

ROTATING X-RAY DETECTOR

The rotating X-ray detector assembly comprises the phosphor detector screen 285, the rotating mirror 290, and the rotating mirror 292. The rotating X-ray detector assembly also comprises the turntable 295 which is supported by the bearings 297. In this embodiment, the phosphor detector screen 285 is advantageously deposited directly onto the window 287 within the vacuum tube 275 so that the X-rays 400 do not have to pass out of the vacuum chamber 275 through the window. Since the window 287 would be likely to attenuate the X-rays 400, depositing the phosphor screen directly onto the inside of the window 287 prevents degradation and absorption of the X-ray image. Instead, the X-rays 400 are first converted to visible light 402, which is not significantly attenuated by the window 287, so that a high quality image is retained.

As described in reference to FIGS. 1-5, an X-ray image of the region 250 of the integrated circuit specimen 210 is formed on the fluorescent screen 285 by X-ray beam 400. Screen 285 converts these X-rays 400 to optical signals 402 for detection by conventional optical devices. In the preferred embodiment, the optical signals 402 from the fluorescent screen 285 are detected by the closed circuit TV (CCTV) camera 300. Camera 300 converts the optical signals 402 to electrical signals for further processing by computer systems 350 and 360. The optical image formed on the screen 285 rotates on the screen in synchronization with the detecting mirror 290. In order to eliminate the need for mechanical motion of the CCTV camera 300 which views the rotating optical image, the optical image is derotated by the optical mirrors 290 and 292 so that the rotating optical images formed on the screen 285 appear stationary as viewed by the camera 300.

Figure 14:
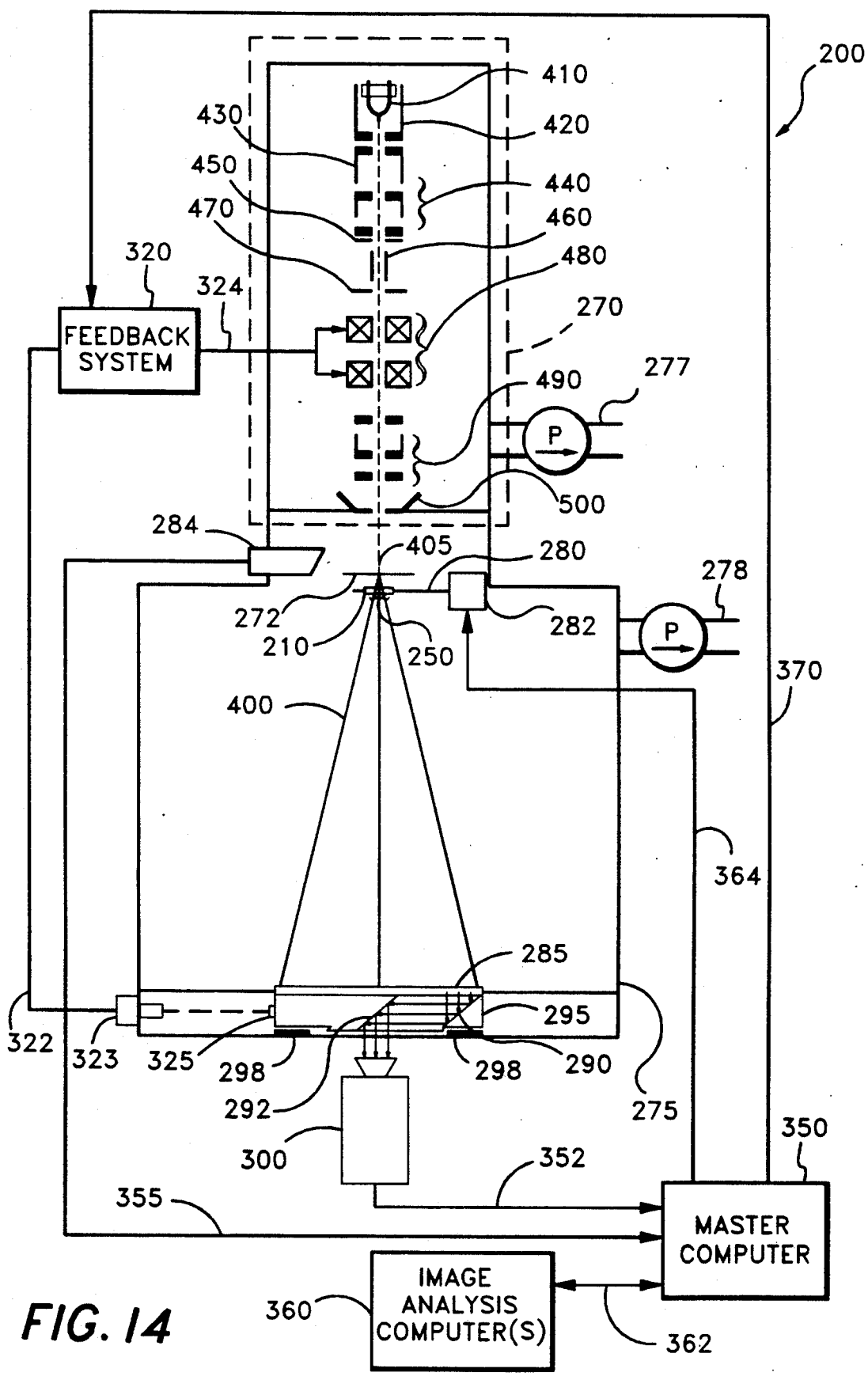
FIG. 14 is a simplified schematic diagram of an alternative embodiment of the high resolution laminography system shown in FIG. 5.

The turntable 295 is mechanically rotated at a uniform angular velocity in a plane which is substantially parallel to a plane defined by the circular motion of the moving X-ray source, and is suspended by means of the bearings 297. Of course it is possible, in an alternative embodiment, to place the turntable 295 within the vacuum chamber 275. In this embodiment, shown in FIG. 14, the turntable 295 would be supported by magnetic levitation bearings 298. The magnetic levitation bearings 298 would advantageously be shielded in a conventional manner so that the magnetic field produced by the bearings 298 does not interfere with magnetically sensitive elements within the laminography system0.

The two mirrors 290 and 292 are mounted within the turntable 295 parallel to one another and at an angle of 45° with respect to the axis of rotation of the turntable 295. The mirror 292 is mounted in the center of turntable 295 so that it intersects the axis of rotation of the turntable 295 near the center of the mirror 292. The mirror 290 is mounted within the turntable 295 so that it faces both the mirror 292 and the fluorescent screen 285. The mirrors 292 and 290 are attached to turntable 295 so that the turntable, and mirrors rotate as a single unit. This arrangement of mirrors, turntable, and screen forms an optical derotation assembly for optical images formed on the screen 285 when the mirrors 290 and 292 are rotated in synchronization with the X-ray source.

An X-ray shadow image of the region 250 of the integrated circuit 210 is formed on the fluorescent screen 285 when the X-ray beam 400 strikes the screen. The fluorescent screen 285 functions as an X-ray to optical converter. For example, when X-rays 400 strike the surface of the screen 285 which faces the X-ray source, visible light 402 is emitted from the screen surface opposite the X-ray source. Optical signals 402 emitted from the fluorescent screen 285 are reflected by the two parallel mirrors 292 and 290 into the lens of the closed circuit TV camera 300.

The mirrors 292, 290 reflect the optical image from the fluorescent screen 285 into the stationary camera system 300 so that the rotation of the image on the fluorescent screen 285 is not apparent to the camera 300. A similar mirror arrangement has been previously described in U.S. Pat. No. 2,998,511 entitled "Tomoscope."

In a preferred embodiment, the fluorescent screen 250 comprises Gadolinium Oxysulfide, $Gd_2O_2S$ coated to a thickness of approximately 0.002 inches. Gadolinium oxysulfide is a scintillation material which is persistent so that it provides high intensity light when hit by an X-ray beam.

CROSS-SECTIONAL IMAGE FORMATION

As previously discussed, a cross-sectional image of the integrated circuit specimen 210 is obtained as the mirrors 290 and 292 derotate the image formed on the screen 285 in synchronization with the X-ray source. The blurring effects of objects outside of the focal plane caused by the laminography method and image resolution of objects within the focal plane are maximized when the cross-sectional image is acquired during a full rotation of the detecting mirror 290 and source. The camera system 300 detects the development of the cross-sectional image on the fluorescent screen 285 by means of the optical derotation assembly comprising the turntable 295, and mirrors 290, 292.

Since the fluorescent screen 285 may not emit high intensity optical signals 402, it is often advantageous to detect the optical signals 402 with a high sensitivity, low light level device. Use of a low light level detection device thus improves the detected image quality by detecting a larger portion of the optical signals 402 emitted from the fluorescent screen 285 during a single rotation of the X-ray source. Many low light level camera systems incorporate an image intensifier as part of the camera system to improve the low light level sensitivity. One particular system is known as a silicon intensified target (SIT) camera and is capable of detecting extremely low levels of light. SIT camera systems are well known and readily available. A preferred embodiment of the present invention utilizes a SIT camera system which is based upon the RCA Model No. 4804BHP2-12 SIT tube.

In a preferred embodiment, one cross-sectional image is acquired in approximately 60 seconds during the rotation of the mirrors 290, 292 and the X-ray source at the rate of approximately 7 revolutions per minute. During one complete revolution, 255 video frames, each frame having a duration of 1/30 second, are collected by the camera 300. The 255 video frames are communicated from the camera 300 to master computer 350 where the 255 frames are averaged together, thus forming a digital representation of the cross-sectional image of the integrated circuit 210 formed on the fluorescent screen 250 during rotation of the X-ray source and turntable 295. Alternatively, the camera 300 may be connected to a CRT, so that the cross-sectional image can be viewed directly.

SOURCE/DETECTOR SYNCHRONIZATION

Figure 7:
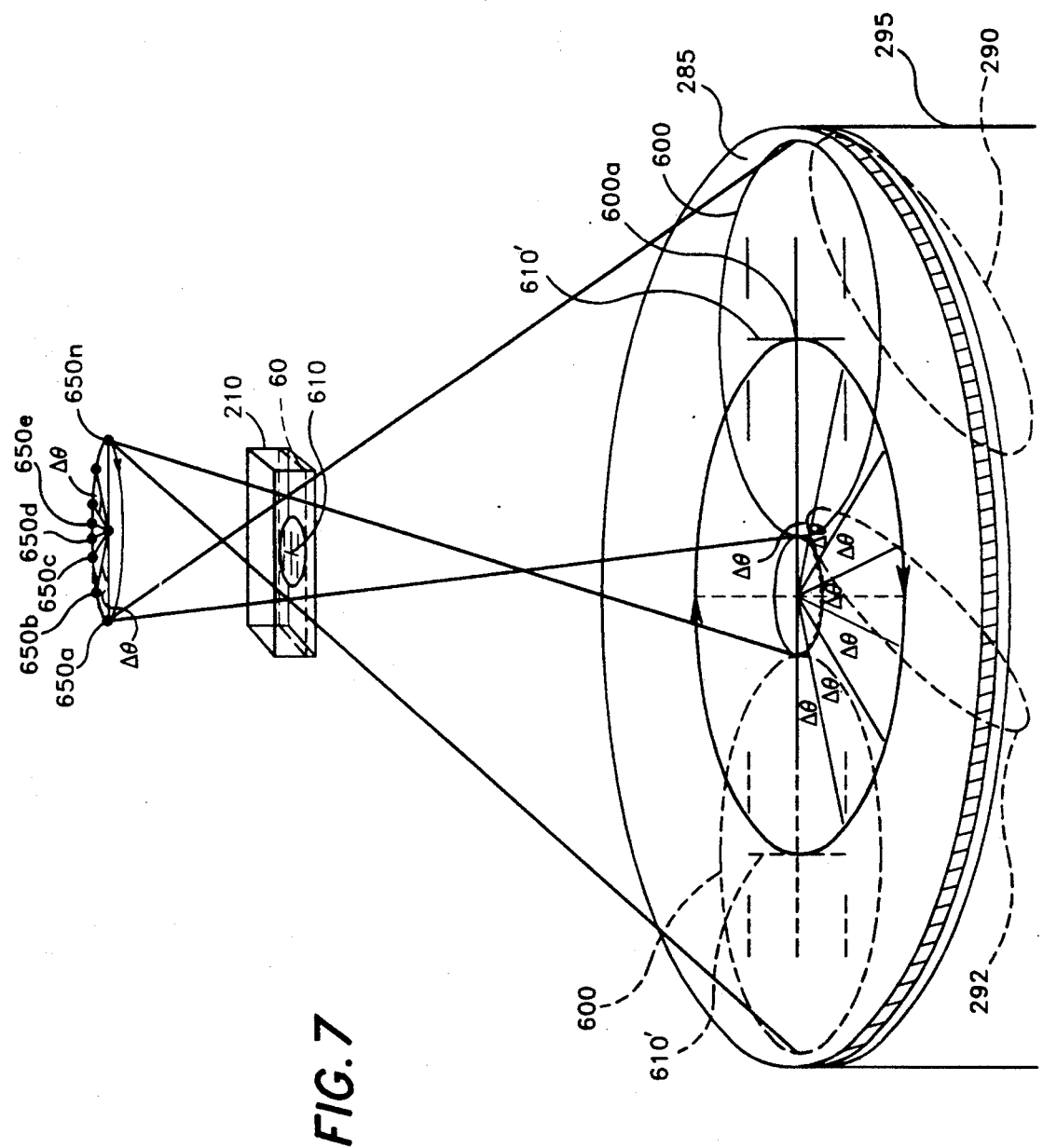
FIG. 7 is a schematic diagram illustrating the calibration procedure for synchronizing the X-ray source and detector positions.

Formation of a high resolution laminographic cross-sectional image depends upon the precise alignment and synchronization of the circular motions of the radiation source and detector mirror 290. As illustrated in FIG. 7, the detector mirror 290 reflects light emitted from a circular portion of the fluorescent screen 285 to produce an effective rotating field of view image 600 on the screen 285. Of course, if the mirror 290 were shaped differently (e.g., in the shape of a square), the rotating field of view image 600 would have a correspondingly different shape. Proper alignment and synchronization between the X-ray source and the detector mirror 290 are achieved when an image formed on the fluorescent screen 285 moves in a circular pattern so that it is stationary with respect to the rotating field of view image 600. Thus, when the X-ray source and the mirror 290 are synchronized, the derotated image formed within the rotating field of view image 600, and reflected into the camera 300, will remain in a fixed position. For the configuration shown in FIG. 7, this is clearly achieved when the angular positions of the source and rotating field of view image 600, relative to a fixed reference position, are separated by 180°.

The preferred alignment and synchronization of the source and the detector mirror 290 are maintained by the feedback system 320 shown in FIG. 5. The position of the rotating turntable 295, wherein the mirror 290 is mounted, is monitored by the sensor 323. The turntable position is communicated to the feedback system 320, which supplies drive signals corresponding to the position of the turntable to the electron beam deflection coils 480. The drive signals control the position of the X-ray source such that the source and mirror 290 are always in alignment as the turntable 295 rotates. In this manner, the feedback system 320 maintains the precision geometry necessary for the production of high resolution cross-sectional images. This system compensates for alignment inaccuracies of the electron focusing column 270 and rotating turntable 295; machining, mounting and fabrication inaccuracies and defects of the target anode 272 and its surface coating; aberrations, such as astigmatism, in the electron beam 405 path through the focusing column 270; and variations in the rotational velocity of the rotating turntable 295 during image formation.

Figure 8:
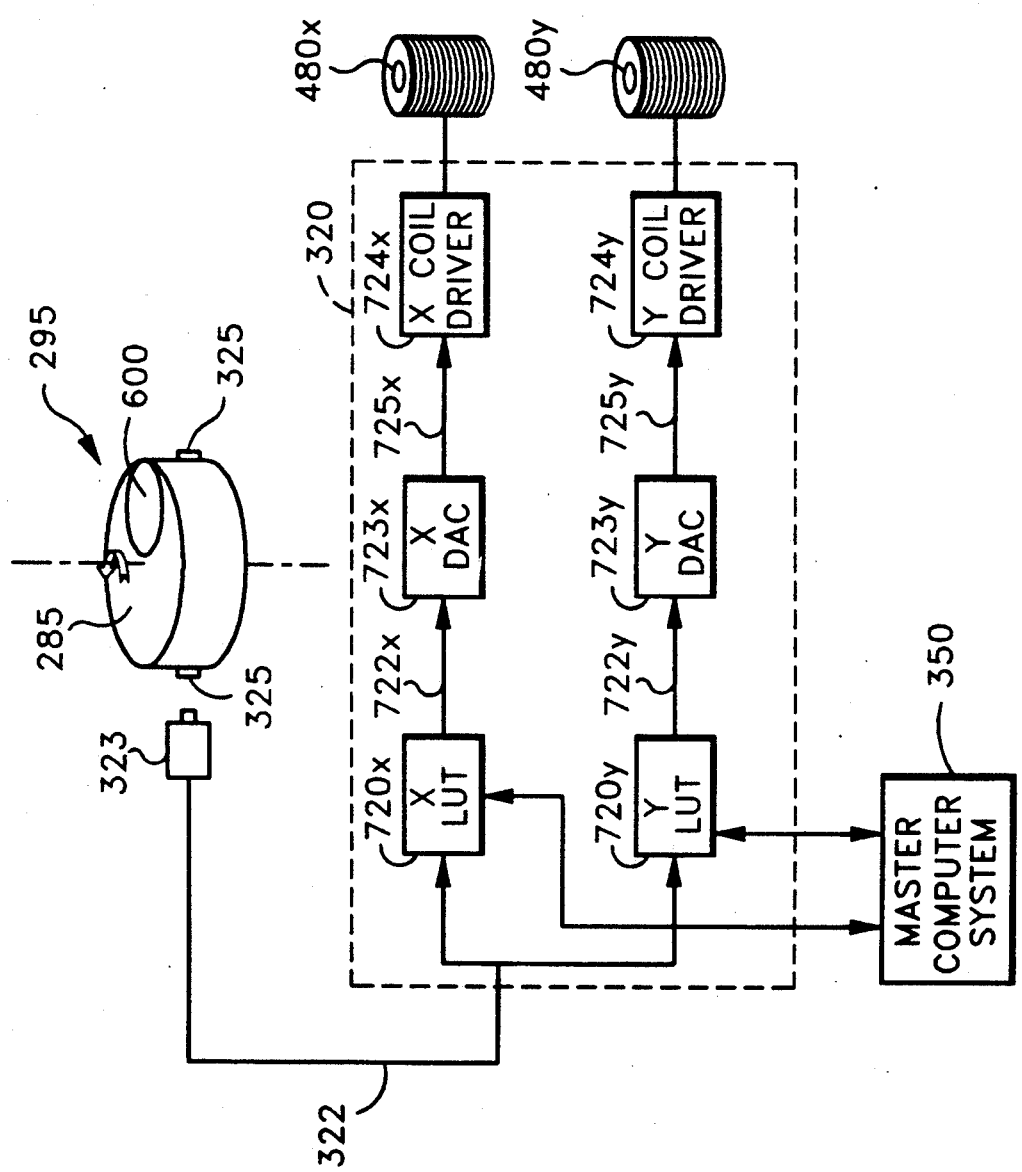
FIG. 8 is a schematic block diagram of the feedback control system used for synchronization of the X-ray source and detector motions.

A detailed block diagram of feedback system 320 is shown in FIG. 8. Feedback system 320 comprises X and Y look-up tables (LUT's) 720X and 720Y, respectively, X and Y digital-to-analog converters (DACs) 723X and 723Y, respectively, and X and Y coil drivers 724X and 724Y, respectively. The LUTs 720X and 720Y are preferably solid state, digital random access memories (RAM). The feedback system links the rotating turntable 295 to the X-ray tube deflection coils 480 under control of the master computer system 350.

As rotating turntable 295 revolves, the position sensor 323 detects the angular position of the turntable 295 from the position encoder 325. The detected angular position is converted to X and Y address signals which correspond to the angular position of the turntable 295 (and thereby the field of view image 600). The address signals are communicated to the X and Y LUTs 720X, 720Y via the communication line 322. By means of a source/detector alignment calibration procedure, X and Y calibration data are determined and stored in the X and Y LUTs for each angular position of the detector. Thus, there exists a one to one correspondence between the X and Y addresses from the encoder and the X and Y calibration data in the LUT's. The X and Y calibration data are retrieved from the LUT's in the form of electronic digital signals. The electronic digital signals are transmitted from the X and Y LUTs to the X and Y DACs 723X and 723Y, respectively, via communication lines 722X and 722Y. The DACs convert the digital signals into analog electrical signals which travel via lines 725X and 725Y to the coil drivers 724X and 724Y. The coil drivers amplify their respective analog input signals and apply resulting output signals via lines 726X and 726Y to the coils 480X and 480Y, respectively, to achieve the precise deflection of the electron beam 405 required for proper alignment of the source and detector mirror. The electron beam 405 is deflected through interaction with magnetic fields generated by the application of the output signals to the coils 480. As the electron beam traverses the magnetic fields, it is deflected, thus moving the position of the X-ray source spot on the target anode 272. The distance the spot moves is proportional to the magnitude of the drive signals as determined by the calibration data.

In one embodiment, the LUT calibration data are determined using preselected trace patterns 610 formed within the integrated circuit specimen 210, as shown in FIG. 7. The location, shape, and dimensions of the preselected trace patterns 610 are advantageously known prior to initiation of the calibration procedure. The integrated circuit 210 is interposed between the X-ray source and the screen 285, so that an X-ray shadowgraph image 610' of the region containing the preselected trace pattern 610 is formed within the field of view image 600. An optical representation of the image 610' formed on the screen 285 is viewed by the camera 300. An electrical representation of the optical image is output from the camera 300, along line 352 to the master computer 350, and the image analysis computer 360. The electrical signals along the line 352 are digitized by the computer 350 and are stored in digital format in the memory of computer 350. Note that the trace pattern 610, and corresponding shadowgraph image 610' shown in FIG. 7 are an exemplary configuration used for the purposes of this illustration. It will be understood that other configurations having distinguishable features may also be used in order to calibrate the X-ray source and detector. Other embodiments that provide a distinguishable fiducial image may also be employed to calibrate the rotation of the source and detector. For example, a test coupon (not shown) having a known pattern formed thereon may be interposed between the source and detector mirror 290 so that the test coupon serves as a fiducial element. The procedure for calibrating the source and detector using a test coupon is substantially the same as the calibration procedure described in U.S. Pat. No. 4,926,452. In another embodiment, a circular trace pattern may be etched onto the target 272. The electron beam 405 is then deflected so that it strikes the target only on the etched circular portion. This causes the X-ray source to follow a corresponding circular trace path.

As shown in FIG. 9, a rectangular portion of the image 610', delineated by the lines 640a through 640d, defines a region of interest 640 which surrounds the images formed by traces 642 in the trace pattern 610. The region of interest 640 is stored in digital format within the memory of the computer 350. As is well known, digitally stored images comprise an array of pixels, each pixel representing a small portion of the image. Specifically, region of interest 640 is divided into a pixel grid comprising 512 columns along border 640a and 480 rows along border 640b. Each pixel in the grid may be represented by its corresponding column and row designation. For example, the lower left corner of region of interest 640 is represented by the pixel (0,0). Similarly, the lower right corner is represented by pixel (511,0), the upper right corner is represented by pixel (511,479) and the upper left corner is represented by pixel (0,479). The center location 660 is represented by pixel (256,240). In one embodiment, the distance between the lower left and lower right corners of the region of interest 640 corresponds to approximately 1.2 mils within the integrated circuit 210. Likewise, the distance between the lower left and upper left corners of the region of interest 640 corresponds to approximately 1.1 mils within the integrated circuit 210.

Determination of the calibration data for the X and Y LUTs is performed either manually or automatically using the trace pattern 610. Referring again to FIGS. 5 and 7, an initial alignment of the X-ray source, integrated circuit 210, turntable 295, and camera 300 is performed manually. First, the integrated circuit 210 is positioned so that the trace pattern 610 falls within the imaged region 250. The X-ray source, the turntable 295 and the camera 300 are then aligned so that the test pattern image 610', formed on the screen 285, is continuously within the field of view image 600 throughout a complete revolution of the source and turntable 295. After the system is thus aligned, the turntable 295 is positioned at an initial angular position defined as $\theta = 0°$. In this initial position, the center pixel (256,240) of the digital image detected by the camera 300 and stored in the computer 350 corresponds to a location 660a within the field of view image 600 on the screen 285. The source is positioned at a location 650a which corresponds to an angular position of approximately $\theta = 180°$, thus placing the trace pattern image 610' within the field of view image 600. If the image center 660a of the trace pattern image 610' does not fall within the center pixel (256,240), then the X and Y deflection values are adjusted to change the position 650a of the source, which in turn changes the location f the image center 660 on the screen 285. The deflection values are adjusted until the image center 660a is caused to be precisely located at center pixel location (256,240). These deflection values are then stored in the LUT's 720 as the calibration data for the turntable 295 position $\theta = 0°$. Turntable 295 and screen 250 are then moved to a new angular position corresponding to an angle $\theta = \Delta\theta$. The X-ray source is moved to a position 650b corresponding to an angular position of approximately $\theta = \Delta\theta + 180°$, thus placing the test pattern image 610' within the field of view image 600. If the image center 660a of the test pattern image 610' does not fall within the center pixel (256,240), then the X and Y deflection values are adjusted to change the position 650b of the source so that the image center 660a is again caused to be precisely located at center pixel location (256,240). These deflection values are then stored in the LUT's as the calibration data for the turntable 295 position $\theta = \Delta\theta°$. This procedure for determining the LUT calibration data is continued in increments of $\Delta\theta°$ until the source and turntable 295 have completed one revolution.

In one embodiment, the calibration procedure experimentally determines the X and Y deflection values necessary to precisely align the source and the detector mirror 290 for 18 equally spaced points along one rotation of the turntable 295. The 18 pairs of calibration "coordinates" are then stored within the memory of the master computer 350. The computer 350 advantageously has access to a curve fitting program which determines the constants of a calibration function for both the X and Y calibration "coordinates" so that the functions exactly fit the 18 pairs of calibration "coordinates." The curve fitting program accepts as input the 18 pairs of "coordinates," and performs a least squares fit to the theoretically calculated curve. If all 18 points do not exactly fit the theoretical curve, then the program automatically adjusts the constants in the theoretical equation to more closely approximate a curve which fits all 18 points. This procedure is repeated until all 18 points are fitted to the theoretical curve (i.e., the least squares fit is equal to zero).

The calibration functions are advantageously sinusoidal (i.e., comprising fundamental and/or harmonic terms of a sine or cosine wave), so as to facilitate generation of calibration signals which correspond to the calibration functions. For example, in one preferred embodiment, the calibration functions are:

$$X_i = A + B\sin(\theta + \Phi_1) + C\sin^2(\theta + \Phi_2) + D\sin^3(\theta + \Phi_3) + \quad (1)$$
$$E\sin^4(\theta + \Phi_4) + F\sin^5(\theta + \Phi_5)$$

$$Y_i = G + H\cos(\theta + \phi_1) + I\cos^2(\theta + \phi_2) + J\cos^3(\theta + \phi_3) + \quad (2)$$
$$K\cos^4(\theta + \phi_4) + L\cos^5(\theta + \phi_5),$$

where A ... L, $\Phi_1$ ... $\Phi_5$, and $\phi_1$ ... $\phi_5$ are all constants determined by the curve fitting program within the master computer 350, and $X_i$ and $Y_i$ are the with pair of calibration "coordinates." Note that each equation has a corresponding electrical deflection signal associated with it, which is transmitted to the deflection coils 480X and 480Y (the X and Y deflection elements of coil 480 respectively). For example, in this case, A and G represent the voltage amplitudes of DC signals, B and H represent the voltage amplitudes of first order sine and cosine waves having phase shifts of $\Phi_1$ and $\phi_1$ respectively, etc. Thus, a pair of calibrated voltage signals which correspond to the determined calibration functions are applied to the X and Y deflection coils 480.

In one preferred embodiment, the angular increment $\Delta\theta$ is approximately 0.022°, corresponding to approximately 16,384 angular positions in one revolution. In this embodiment, the X and Y LUT's each have at least 16,384 address locations for the storage of deflection data corresponding to each discrete angular position. Thus, for $\theta = 16,384$ multiples of 0.022°, a pair of digital deflection voltages is calculated using equations (1) and (2) and their determined constants, so that each of the 16,384 coordinate pairs fits the curve defined by equations (1) and (2).

As the source and turntable 295 rotate, each address in the X and Y LUT's is sequentially accessed so that the correct X and Y digital deflection voltages are provided to the coils 480X and 480Y for each angular displacement $\Delta\theta$ during the rotation of the turntable 295. The X and Y LUT's are accessed in response to signals from the sensor 323, which detects the angular position of the turntable 295 in increments of 0.022° by means of the position encoder 325. The digital voltages applied to the coil 480 cause the electron beam 405 to deflect to the appropriate spot on the target 272 so that the source and the turntable 295 rotate in precise synchronization. Note that if there were no mechanical aberrations within the laminography system of the present invention, it would not be necessary to determine calibration signals to synchronize the source and detector. Instead, a straight sine wave having a DC level could be applied to the X deflection coil 480X, and a straight cosine wave also having a DC level could be applied to the Y deflection coil 480Y to produce a circular trace path.

FIG. 10 illustrates a basic flow chart of the logical sequence of steps performed by the calibration procedure to determine the X and Y calibration data which are stored in the X and Y LUTs 720 for controlling the deflection coils 480. First, as previously described, the mechanisms of the invention, as shown in FIG. 5, including the electron column 270, turntable 295 with mirrors 290, 292, the target 272 and specimen positioning table (fixture) 280 are assembled and mounted in approximate alignment. Next, the fiducial element (e.g., the test coupon or the integrated circuit 210 having a known trace pattern 610) is mounted to the fixture 280. The piezoelectric stage 282 then moves the fiducial element that the desired magnification of the pattern is obtained.

Figure 10A:
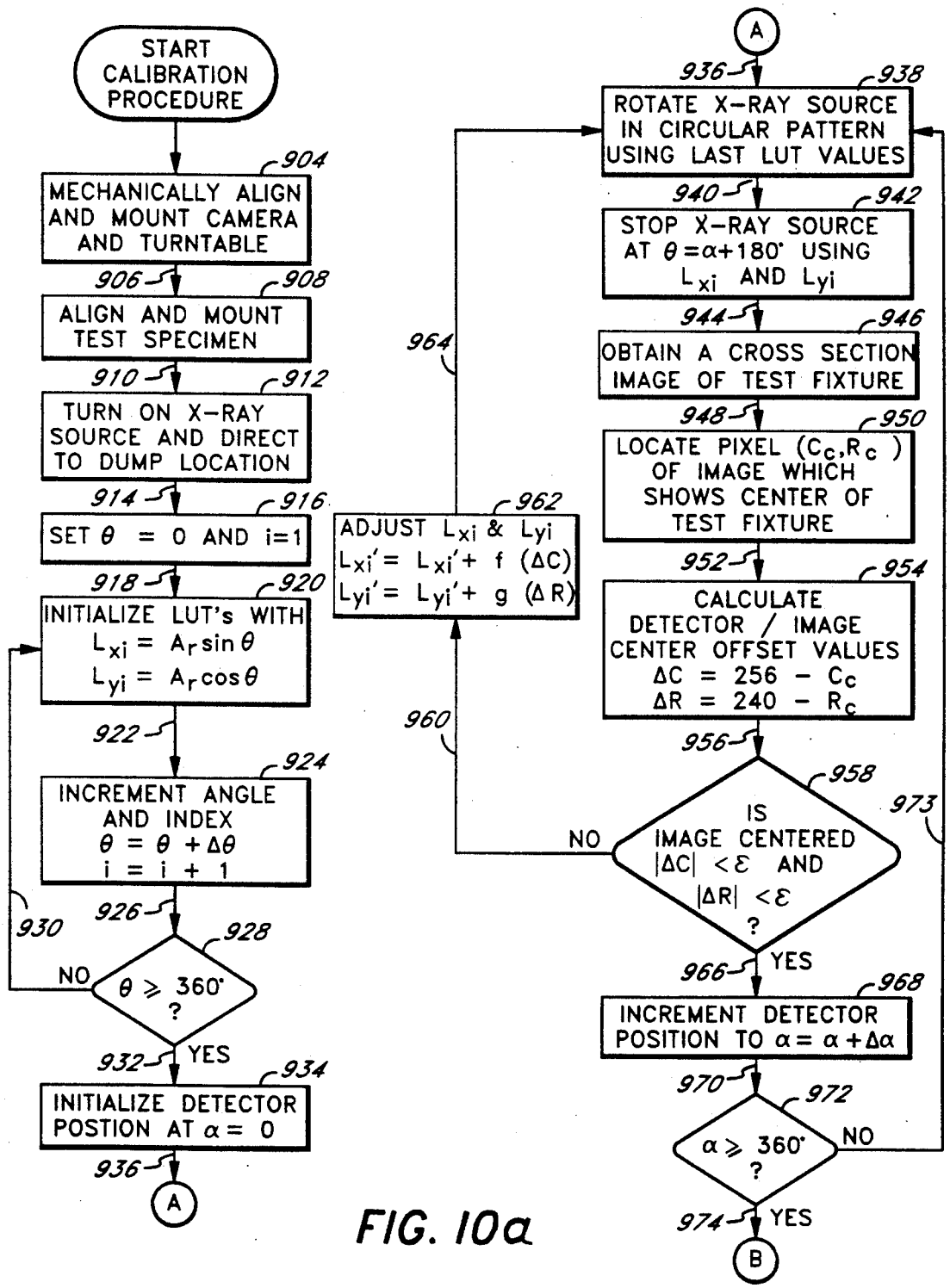
FIGS. 10a and 10b are a flowchart which illustrate the method used to calibrate the source with the detector.
Figure 10B:
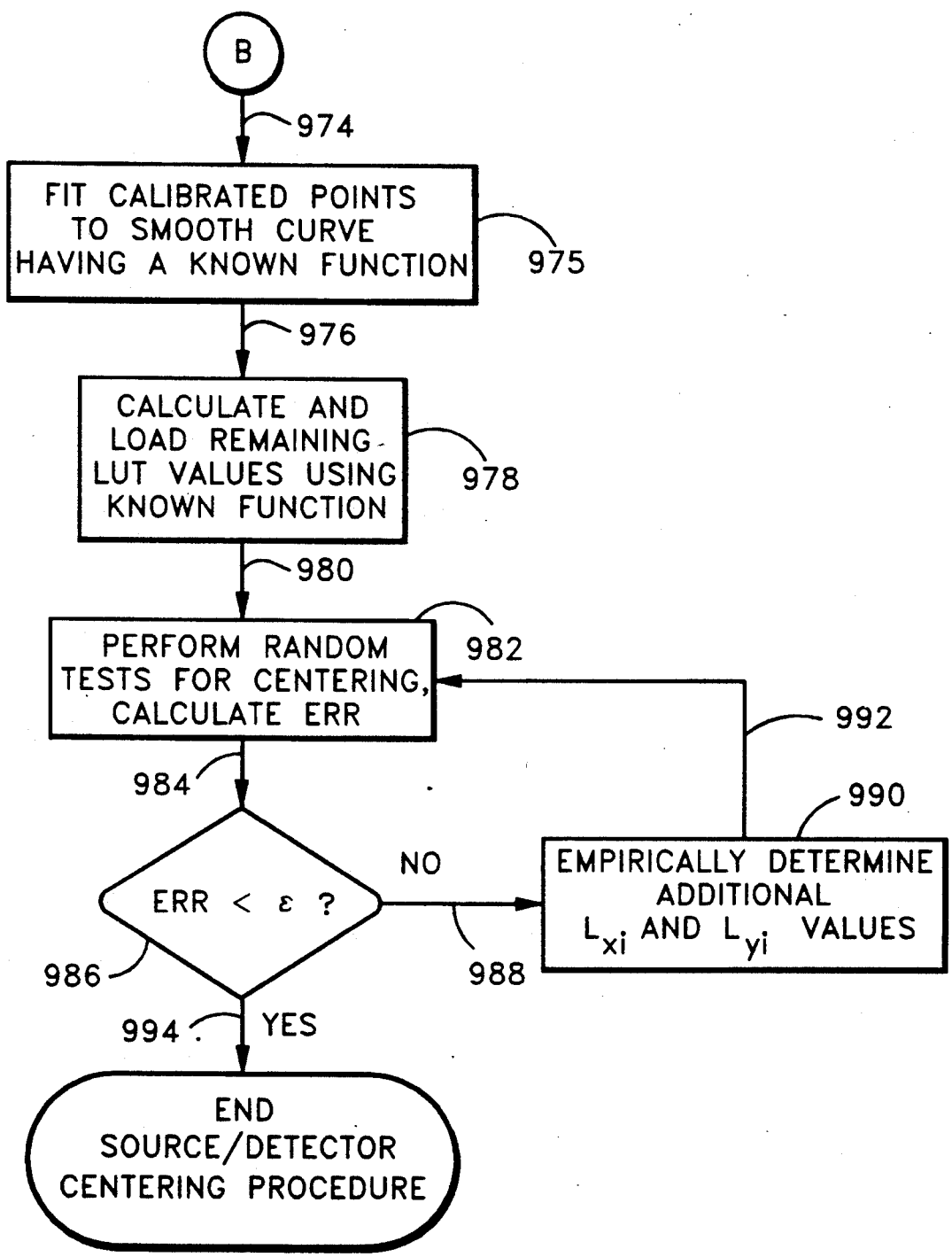

The step of mechanically aligning the camera 300, and the optical assemblies (i.e., the turntable 295 and the mirrors 290, 292) is represented by an activity block 904 in FIG. 10a. Control is passed from activity block 904 via a path 906 to an activity block 908, wherein the test specimen (referred to hereafter as the integrated circuit 210 in reference to FIGS. 10a and 10b) is mounted and aligned on the fixture 280. Control then passes via a path 910 to an activity block 912 wherein the X-ray source is turned on and the electron beam 405 is directed to a beam dump location. Beam dumping is advantageously accomplished using the blanking plates 460 and the blanking aperture 470. Deflection of the beam 405 to a dump location allows the X-ray tube to stabilize without subjecting the integrated circuit 210 and detector to X-rays. Control proceeds via path 914 to an activity block 916 wherein the angular position variable $\theta$ and an address indexing variable i are initialized at $\theta = 0°$ and i = 1, respectively. Control is passed from activity block 916 to activity block 920 via a path 918. Activity block 920 represents the initialization of the LUTs with initial approximations given by $$L_{xi} = A_r \sin\theta \quad (3)$$

$$L_{yi} = A_r \cos\theta \quad (4)$$

where $A_r$ is proportional to the approximate radius of the rotating source and i is the LUT address which contains deflection data corresponding to the angular position $\theta$. activity block 924, reached via path 922 from block 920, the angular position $\theta$ is incremented by an amount $\Delta\theta$ and the index i is incremented by 1. As stated above, in one preferred embodiment, the angular increment is $\Delta\theta$ is approximately 0.022°, corresponding to approximately 16,384 angular positions in one revolution. In this embodiment, the X and Y LUT's each have at least 16,384 address locations for the storage of deflection data corresponding to each discrete angular position, and the addressing index i takes on integral values ranging from 1 to at least 16,384. Control then passes via path 926 to decision block 928. In decision block 928, the value of $\theta$ is checked to see if it is greater than or equal to 360°. If $\theta$ is not greater than or equal to 360°, then control returns to block 920 via path 930. If $\theta$ is greater than or equal to 360°, then control passes via path 932 to activity block 934. The steps from 920 through 928 form a loop wherein all of the available LUT addresses are loaded with initial deflection values which will cause the electron beam 405 to circumscribe a circular path upon the target 272. In the embodiment having 16,384 discrete angular positions, the steps 920 through 928 will be executed approximately 16,384 times.

Upon completion of the LUT initialization process, control passes via path 932 to activity block 934, wherein the detector mirror 292 is positioned at an initial reference location defined as $\alpha = 0°$. Control is then transferred via path 936 to activity block 938, wherein the current data $(L_{xi}, L_{yi})$ stored in the LUT's are used to control the rotation of the X-ray source. When activity block 938 is entered via path 936, the current data in the LUT's are the initial values calculated in accordance with equations (3) and (4) and represent an initial approximation of the final values to be calculated by the below described calibration procedure.

Determination of the LUT calibration data proceeds via a path 940 to activity block 942. In block 942, the rotating X-ray source is stopped at the angular position $\theta$ which is approximately equal to $(\alpha + 180)°$, where $\alpha$ is the angular position of the X-ray detector mirror 292. For example, when the detector mirror 292 is at the initial position $\alpha = 0°$, then the X-ray detector mirror 292 is positioned at angular position $\theta = 180°$ in block 942. In the embodiment having 16,384 angular positions and corresponding LUT addresses, the deflection values stored in LUT memory locations $L_{x8192}$ and $L_{y8192}$ will produce the deflection of the electron beam 405 to the location on the target 272 corresponding to an angular position of the X-ray source of $\theta = 180°$.

Subsequent to stopping the rotating X-ray source at angle $\theta$ in activity block 942, control is passed via line 944 to activity block 946. In activity block 946, the cross-sectional image 610' of trace pattern 610 is obtained and stored in a digital image memory. In a preferred embodiment, the image memory comprises a pixel grid having 512 columns and 480 rows.

A path 948 transfers control from activity block 946 to an activity block 950, wherein the pixel(s) $(C_c, R_c)$ containing the location of the image center 660a of image 610' are located. $C_c$ and $R_c$ are the column and row designations respectively, of the image pixel containing the center of the image, and may be identified manually or automatically by means of computer analysis techniques.

The image center pixel position $(C_c, R_c)$ determined in activity block 950 is transferred to activity block 954 via path 952, wherein the relative offset of the image center from the center of the field of view image 600 is calculated according to the following equations.

$$\Delta C = 256 - C_c \quad (5)$$

$$\Delta R = 240 - R_c \quad (6)$$

$\Delta C$ and $\Delta R$ represent the distance by which the center of the trace pattern image 610, at pixel coordinates $(C_c, R_c)$ is offset from the center of the digital image defined as pixel (256,240).

The $\Delta C$ and $\Delta R$ values calculated in activity block 954 are transferred via path 956 to decision block 958, wherein $\Delta C$ and $\Delta R$ are compared to the value zero. If $\Delta C$ or $\Delta R$ is not substantially equal to zero, i.e., if their absolute values are not less than some arbitrarily small number, $\epsilon$, then the test pattern image center is not coincident with the digital image center and control is passed via path 960 to activity block 962 where the LUT calibration data are adjusted accordingly.

In activity block 962, the LUT calibration data $L_{xi}$ and $L_{yi}$ are adjusted in accordance with the following equations.

$$L_{xi}' = L_{xi} + f(\Delta C, \Delta R) \quad (5)$$

$$L_{yi}' = L_{yi} + g(\Delta C, \Delta R) \quad (6)$$

Mathematical functions $f(\Delta C, \Delta R)$ and $g(\Delta C, \Delta R)$ are used to calculate the magnitude of adjustments for the LUT values $L_{xi}$ and $L_{yi}$ respectively, which will reduce the centering errors $\Delta C$ and $\Delta R$. The values $L_{xi}$ and $L_{yi}$ in the LUT's are replaced with the adjusted values $L_{xi}'$ and $L_{yi}'$ respectively. These adjusted LUT values are transmitted to the activity block 938 via line 964 and a first loop comprising the steps 938, 942, 946, 950, 954, 958, and 962 is re-executed until the image center 660a is substantially coincident with the digital image center. When the image 610' is centered, $\Delta C$ and $\Delta R$ are substantially equal to zero and control passes from decision block 958 via path 960 to activity block 968.

In block 968, the detector position is incremented by the amount $\Delta \alpha$ to the next angular position ($\alpha + \Delta \alpha$). The new angular position of the detector is passed via path 970 to decision block 972 to determine if the new angle $\alpha$ is greater than or equal to 360°. If $\alpha$ is less than 360°, then control passes via path 973 to activity block 938. A second loop comprising the first loop and additional steps 968 and 972 is re-executed until the detector has completed one revolution, i.e., when $\alpha$ is greater than or equal to 360°.

In a preferred embodiment, the angular increment $\Delta \alpha$ is selected to be substantially larger than the angular increment $\Delta \theta$ between successive entries in the LUT's so that a calibration for a complete revolution can be calculated in a short period of time. For example, if the increment $\Delta \alpha$ is equal to 20°, then a complete calibration can be calculated using 18 equally spaced points about one revolution of the turntable 295. The calibrated 18 points are then fit to a smooth curve, as shown in activity block 975, that may be described mathematically by Equations (1) and (2) in one embodiment. This is advantageously done using a curve fitting program as described above. Once a circular curve which includes all 18 points has been mathematically defined in the activity block 975, control passes via path 976 to an activity block 978. In the activity block 978, the remaining LUT values corresponding to positions intermediate the 18 calculated positions are determined by calculating the appropriate voltage deflection values using Equations (1) and (2), and the known values of $\theta$ for each of the remaining 16,366 (i.e., 16,384-18) angular positions. Control is then passed to activity block 982 via path 980 for random testing of the centering of the image.

In activity block 982, random angular positions are selected where the accuracy of the centering is determined. A centering error, ERR, is calculated which reflects the error of the randomly selected positions. The centering error value is passed via path 984 to decision block 986 wherein the value is compared to zero or some other predetermined value. If ERR is not substantially zero, then control passes via path 988 to activity block 990.

In activity block 990, an error correction deflection signal is determined using the centering error, ERR. This signal automatically compensates for small errors in the LUT values $L_{xi}$ and $L_{yi}$. Once the error signal is generated as indicated in the activity block 990, control returns to the activity block 982 via path 992 so that a random sampling can be taken again, and a new centering error is calculated. This loop continues until ERR is less than the predetermined error threshold value, at which time, control is then passed via path 994 to the end of the calibration procedure.

The starting and stopping of the rotation of the electron beam 405 indicated in blocks 938 and 942 between successive calibration locations serves at least two functions. First, excessive heating of the target 272 is prevented because the rotating electron beam 405 does not strike any one spot on the target for an extended period of time. Second, hysteresis effects in the steering coils 480 are automatically compensated by continuous passage through complete hysteresis cycles. It will be understood that the above calibration procedure can either be performed manually under operator control or automatically under computer control.

It will be understood that other calibration procedures may be used to synchronize the rotation of the X-ray source and detector.

COMPUTER CONTROL AND ANALYSIS SYSTEM

Figure 11:
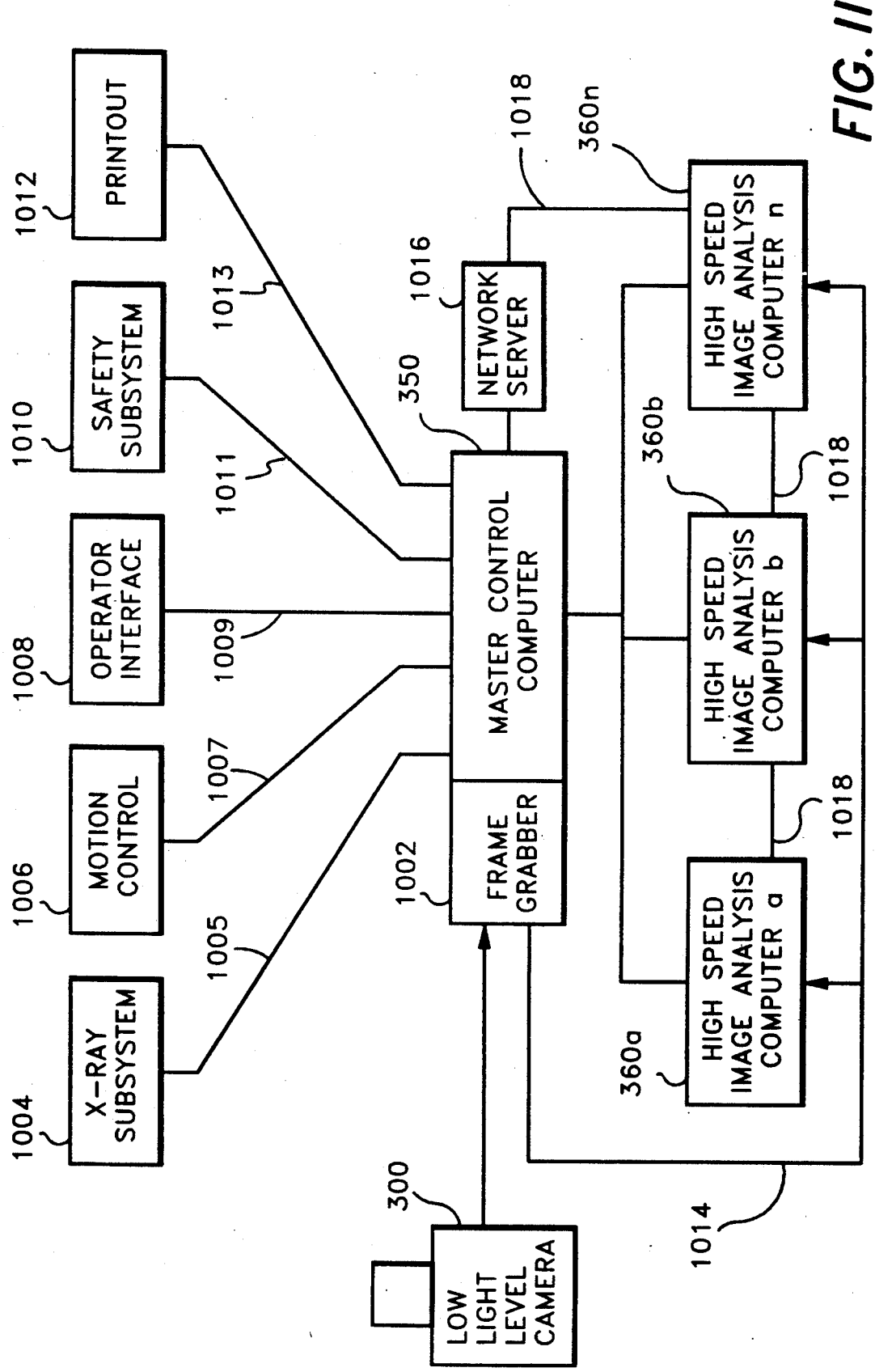
FIG. 11 is a block diagram which shows the major elements of the computer control and analysis system.

FIG. 11 is a block diagram of the computer control and analysis system architecture for the automated laminography inspection system of the present invention. The computer system is centered about the master control computer 350. A video frame grabber 1002 is incorporated into the computer 350 via a plug-in board. The low light level camera 300 is connected to master computer 350 via the line 276. A variety of subsystems, including X-ray 1004, motion control 1006, operator 1008, safety 1010, and printout 1012 communicate with the master computer via communication lines 1005, 1007, 1009, 1011 and 1013, respectively. Multiple high speed image analysis computers 360a, 360b, ..., 360n, also called "analysis engines", communicate with the master computer 350. These communications take the form of "messages" that are passed between the master computer and the analysis engines. The analysis computers 360 also communicate with the frame grabber 1002 via a communication line 1014. In a preferred embodiment, each analysis computer 360 comprises an INTEL ®, Model 303, 386 processor board with an 80386 CPU, 5 megabytes of main RAM memory and a video frame grabber memory. The master computer 350 also comprises an INTEL ®, Model 303, 386 processor board with an 80386 CPU. The analysis computers 360 are connected to the master computer 350 by a Novell Ethernet network which comprises a network server 1016 and a daisy chain connection line 1018.

In operation, the master computer 350 controls the operation of the inspection system through the various subsystems 1004 through 1012. The master computer 350 also controls the acquisition and analysis of the laminographic images from which is derived a measure of the quality of the item under inspection. The master computer automatically controls the operation of the invention in two ways. First, a programmed sequence of movements is executed to acquire digital cross-sectional images. Second, a programmed analysis procedure automatically examines and interprets the digital cross-sectional images. The analysis of one image may be performed simultaneously with the acquisition of a second image. The analysis performed by the master computer system results in an output data listing which categorizes the various defects and other conditions that were detected in the item under examination.

Specifically, for the inspection of circuit traces 212 and electrical connections 214 on integrated circuits 210, the computer 350 controls the motion of the Z-axis translation stage 282 and fixture 280 to which the integrated circuit 210 is mounted, as well as the path followed by the X-ray source. Often the area contained within one cross-sectional image, for example 1.2 mils × 1.1 mils, is smaller than the total area of the integrated circuit or other item to be inspected. In this case, the item is logically represented by multiple X-Y fields of view which, when combined, include the total inspectable area of the integrated circuit 210. The master computer positions each X-Y field of view for inspection by issuing appropriate deflection signals to the deflection coils 480. The deflection signals issued to the deflection coils 480 are advantageously DC voltage levels which cause the path traced by the electron beam 405 on the target 272 to shift horizontally in the X and/or Y directions. The magnitude of the DC voltage levels applied to the coils 480X and 480Y are proportional to the distance that the path traced by the electron beam 405 is shifted. Because the X-ray source is coincident with the spot where the electron beam 405 strikes the target 272, shifting the path traced by the electron beam 405, also causes a coincident shift in the path traced by the X-ray source.

FIGS. 2a and 2b clearly illustrate how the imaged region of the focal plane 93 can be shifted in the X and Y directions by shifting the circular path traced by the X-ray source 20 in the X and Y directions. FIG. 2a shows the X-ray source 20 following a circular path A so that an image 81' of the arrow pattern 81 is produced on the detector 30 throughout an entire rotation of the detector 30. Note that X-rays from the X-ray source 20 also cause an image 82' of the cross pattern 82 to be formed, however, the image 82' does not fall onto the detector throughout an entire rotation so that the cross pattern 82 in the focal plane 93 is not clearly imaged. FIG. 2b shows the X-ray source 20 following a circular path B which is shifted horizontally from the path A (shown in phantom), so that the image 82' of the cross pattern 82 is produced on the detector 30 throughout an entire rotation of the detector 30. Note that X-rays from the X-ray source 20 also cause the image 81' of the arrow pattern 81 to be formed, however, the image 81' does not fall onto the detector throughout an entire rotation so that the arrow pattern 81 in the focal plane 93 is not clearly imaged. Thus, deflection voltages issued by the master computer 350 to the deflection coils 480X and 480Y via the feedback system 320, allow the high resolution laminography system of the present invention to inspect multiple XY fields of view which, when combined, include the total inspectable area of one focal plane within the integrated circuit 210.

After an XY field of view is in position for inspection, the resulting cross-sectional image is acquired and integrated in the camera 300. The video signal of the image is then transmitted from the camera to the high speed image analysis computer 360. Specific Z locations may also be imaged within the integrated circuit 210 in order to bring different planes of the traces 212 and electrical interconnections 214 into focus in the resulting cross-sectional images.

In order to image different horizontal planes along the Z direction within the integrated circuit 210, the master computer 350 issues deflection signals to the coils 480X and 480Y which cause the radius of the circular path traced by the electron beam 405 on the target 272 to vary. This is advantageously accomplished by simultaneously varying the magnitude of the first order sine signal applied to the X deflection coil 480X, and the first order cosine signal applied to the Y deflection coil 480Y. The change in magnitude of the first order sine and cosine signals is proportional to the change in radius of the circular path traced by the electron beam 405. As stated above, because the X-ray source is coincident with the spot where the electron beam 405 strikes the target 272, shifting the path traced by the electron beam 405, also causes a coincident shift in the path traced by the X-ray source.

FIGS. 3a and 3b clearly illustrate how regions within different focal planes along the Z-axis can be imaged by varying the radius of the circular path traced by the X-ray source 20. FIG. 3a shows the X-ray source 20 following a circular path A, so that an image 81, of an arrow pattern 81 is formed on the detector 30 throughout an entire rotation of the detector 30. The arrow pattern 81 is imbedded within the integrated circuit 210 in a focal plane 105. FIG. 3b shows the X-ray source 20 following a circular path B, having the same axis of rotation but a smaller radius than the path A, so that an image 82' of the cross pattern 82 is formed on the detector 30 throughout its entire rotation. The cross pattern 82 is imbedded within the integrated circuit 210 in a focal plane 106. The focal plane 106 is displaced by a distance $\Delta Z$ from the focal plane 105, corresponding to a change in radius, $\Delta R$, of the path traced by the X-ray source 20. Thus, deflection signals issued by the master computer 350, which produce a change in the radius of the circle traced by the X-ray source, allow the high resolution laminography system of the present invention to image and inspect fine slices along the Z axis of the integrated circuit 210.

In addition to the fine slicing in the Z direction accomplished by varying the radius of the path traced by the X-ray source, coarse translation of the integrated circuit 210 may be accomplished by means of the piezoelectric translation stage 282. The master computer 350 transmits a DC voltage level to the stage 282 to cause a piezoelectric crystal within the stage 282 to expand or contract. The fixture 280 is attached to the piezoelectric crystal, thereby resulting in a Z-axis translation of the fixture 280 and the mounted integrated circuit 210. The distance of translation of the integrated circuit 210 is proportional to the voltage applied to the piezoelectric stage 282, and can typically be on the order of a micron. This coarse adjustment of the integrated circuit 210 allows the high resolution laminography system of the present invention to provide different magnifications of the imaged regions within the integrated circuit.

As is known to those skilled in the art, magnification of a laminographic image is dependent upon the source to focal plane distance and the source to detector distance. Namely, the magnification achieved by a laminographic system is equal to the source to detector distance divided by the source to focal plane distance. Heretofore, high magnifications have been achievable, however the resolution necessary to accurately inspect the imaged object has not been obtainable. The present invention provides a high resolution laminography system which allows accurate inspection of images with magnifications up to 10,000 times. In one embodiment, the distance between the target 272 and the detecting phosphor screen 285 is approximately 30 inches, while the distance between the source and the focal plane within the integrated circuit 210 may be varied from 1-100 mils. In order to image a field of view of approximately 1.2 mils×1.1 mils, at a typical magnification of 5,000, the diameter of the effective field of view image 600 should be approximately 9 inches. In one embodiment, the radius of the path traced by the field of view image 600 is approximately 10 inches.

The preferred scan sequence for an integrated circuit is to collect all of the required Z level images for a fixed XY location, then move to the next XY location and collect all of the required Z level images for that location. This step and repeat sequence iterates until all necessary areas and levels of the integrated circuit 210 have been imaged and analyzed.

The fully automated inspection of all traces 212 and electrical interconnections 214 within the integrated circuit 210, performed under the control of the master computer 350, utilizes a preprogrammed inspection routine, custom tailored for the specific integrated circuit design being inspected. The integrated circuit 210 is scanned, and each trace 212 and electrical interconnection 214 is examined through the acquisition and analysis of cross-sectional images.

Figure 12:
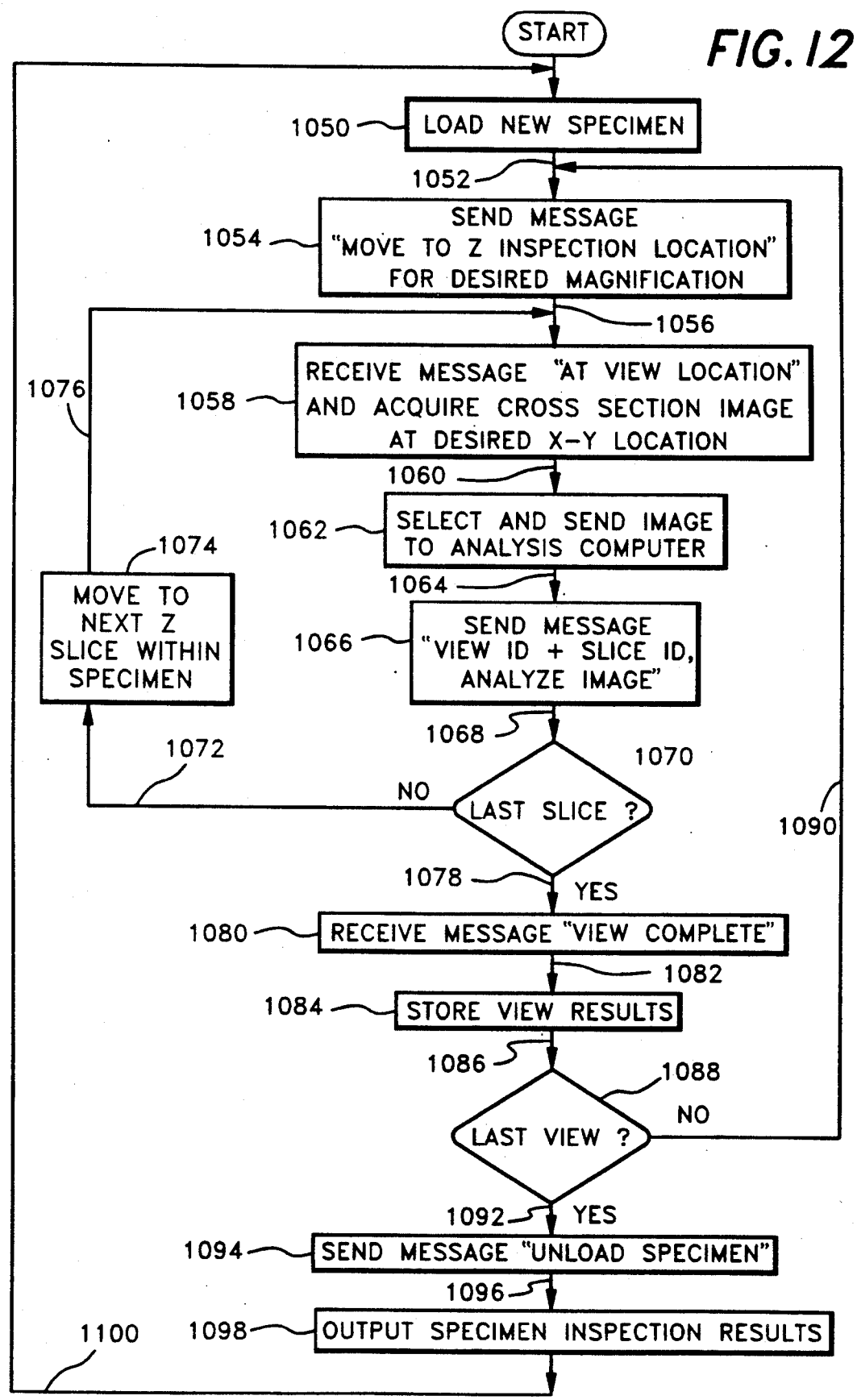
FIG. 12 is a flowchart that illustrates the method used to inspect the different regions of a specimen under examination.

A flow chart illustrating the steps of this automated inspection routine is shown in FIG. 12. Beginning in activity block 1050, the integrated circuit 210 for inspection is inserted into the load/unload port of the invention. The load/unload port (not shown) is advantageously constructed to be similar to the load/unload ports employed in conventional electron microscopes that input a specimen to be imaged. Control is then transferred via path 1052 to activity block 1054 wherein the master computer 350 sends signals to the piezoelectric translation stage 282, which cause the fixture 280, and mounted integrated circuit 210 to move to the desired Z position. This provides the desired magnification of the inspected region of the integrated circuit 210.

Proceeding via path 1056, the routine enters a first loop comprising activity blocks 1058, 1062, 1066, 1070 and 1074. In activity block 1058, the master computer receives a message that the integrated circuit 210 is at the desired magnification. The master computer then sends deflection signals to the coils 480X and 480Y, and controls the detector subsystem such that a cross-sectional image of the IC at a first XY view location, and a first Z slice within the integrated circuit 210, is acquired. That is, the circular path traced by the X-ray source is shifted to the appropriate X and Y position, and the radius of the trace path is varied to obtain a cross-sectional image at a desired Z slice within the integrated circuit 210. After the cross-sectional image is acquired; control passes via path 1060 to activity block 1062 wherein the previously acquired cross-sectional image is sent to one of the analysis computers 360.

Proceeding via path 1064 to activity block 1066, a message is received by the analysis computer 360 which uniquely identifies the view and slice represented by the received image. The image is then analyzed by the analysis computer, while the master computer program proceeds via path 1068 to decision block 1070. In the decision block 1070, the identity of the most recently acquired Z slice is checked to see if that is the last Z slice to be taken at that XY view location. If more Z slices are required, control passes via path 1072 to activity block 1074. In block 1074, the master computer 350 sends signals to the coils 480 which cause the radius of the path traced by the X-ray source to change so that the focal plane moves in the Z direction within the integrated circuit 210 and the next Z slice is acquired. Control then proceeds via path 1076 back to activity block 1058. Another cross-sectional image is acquired in block 1058, which is sent to an analysis computer 360 in block 1062, and identified and analyzed in block 1066. The first loop, comprising the steps 1058, 1062, 1066, 1070 and 1074, is repeated until it is determined in decision block 1070 that the last Z slice for the current XY view position has been acquired.

When the last Z slice has been acquired, control is transferred via path 1078 to activity block 1080 wherein a message indicates that the inspection of that particular XY view is complete. For example, if a particular XY view requires three different Z level slices, then the first loop will be executed three times, once for each Z level. At the completion of the third execution of the first loop, a message indicates that all data for that XY view has been acquired and analyzed.

Figure 13:
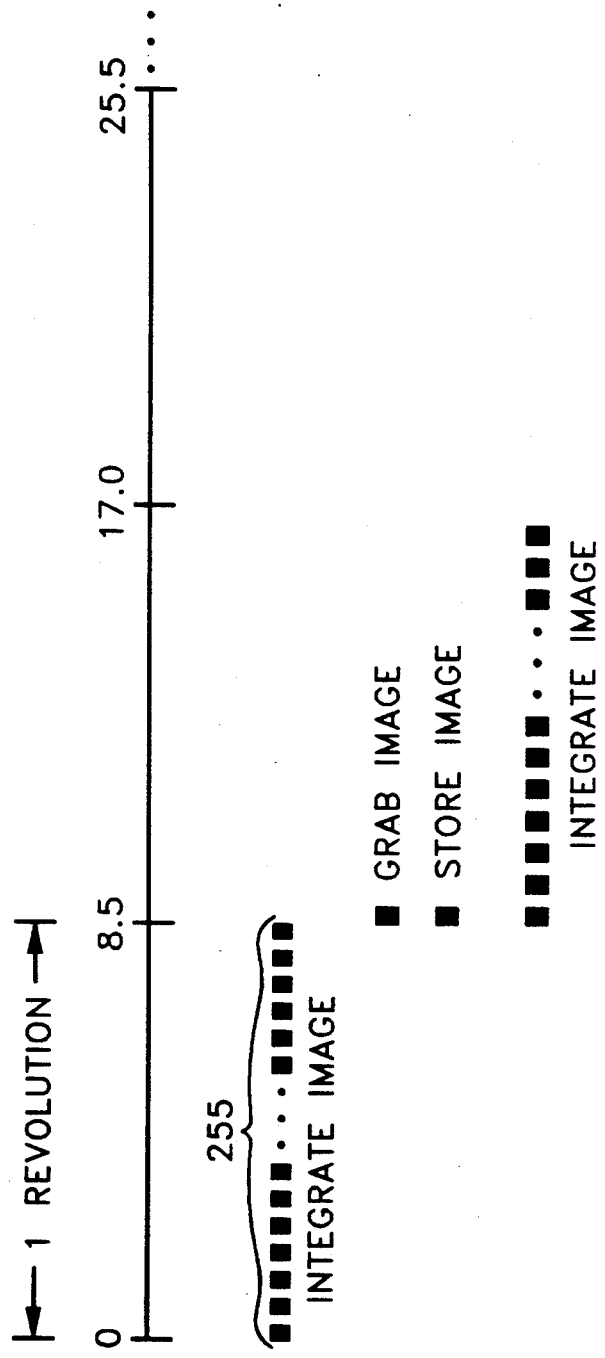
FIG. 13 is a diagram of the timing cycle for the coordinated motion of the source and detector, and image acquisition by the camera and computer system.

In one embodiment of the present invention, a cross-sectional image at a given XY view location and at a given Z slice is acquired and analyzed within 10-60 seconds. An arithmetic image analysis computer board, built by Matrox (not shown) is advantageously incorporated within the frame grabber 1002 (see FIG. 11). The image Matrox board may, for example, include means for integrating up to 255 sequential digital images, such as those transmitted from the camera 300. The camera 300 transmits one complete image frame as sequential video signals in 1/30 second, so that a total of 255 image frames are transmitted by the camera 300 in 8.5 seconds. In one embodiment, this is also the time the turntable 295 takes to complete one rotation. A timing diagram for the steps used in the procedure for acquiring a video image is shown in FIG. 13. The unit of time chosen is one rotation time, or 8.5 seconds, which is the time in which 255 frames are integrated into a single image using the Matrox board. It should be noted that other means of integrating the image may also be used. For example, the camera face plate can be left open over an entire rotation so that integration of the image is automatically accomplished. At the start of the first loop cycle, the integrated circuit 210 is scanned at the desired inspection location, the X-rays are on, and the camera 300 begins to transmit sequential video signals for each of 255 frames over a period of 8.5 seconds. During these 8.5 seconds, the turntable 295 and X-ray source make one complete revolution. When all of the 255 frames have been digitally integrated by means of the Matrox board, digital information corresponding to the integrated image is "grabbed" from the Matrox board, and is stored within the master computer 350. In order to increase the signal to noise ratio, it is sometimes advantageous to acquire multiple integrated images. In such circumstances, multiple sets of 255 frames can be integrated and transferred to the memory of the master computer 350, thus requiring multiple rotations of the turntable 295. Each integrated image set is then digitally averaged with the other integrated images stored within the master computer 350 until a final image is produced. Once a final image is produced, the image is sent to one of the image analysis computers 360 (FIG. 11). Meanwhile, the master computer 360 (FIG. 11) executes a command which causes the X-ray source to trace a different predetermined path in order to image the next view area or slice position for acquisition of another cross-sectional image. In this way, the entire integrated circuit 210 can be imaged with a minimum of mechanical movement. Note also that there are no mechanical vibrations caused by the movement of the X-ray source so that system stability is increased.

One embodiment of the invention performs real time image processing by utilizing the parallel processing analysis computers 360 shown in FIG. 11. The parallel processing architecture enables the system to perform several different activities simultaneously. For example, the system may simultaneously analyze several different images while also acquiring additional images. Thus, the system does not need to wait for each image analysis to be completed before subsequent images can be acquired. The optimum number of analysis computers can be determined, based upon the complexity of the image analyses being performed, such that the image processing computing does not become a bottleneck in the inspection process.

Upon completion of an XY view in block 1080, control is transferred via path 1082 to activity block 1084, wherein the results for that particular XY view inspection are stored in the memory of the master computer. Proceeding via path 1086 to decision block 1088, the XY view identification is checked to determine if additional XY views of the integrated circuit 210 are required.

If additional XY views are required, then control is transferred via path 1090 to activity block 1054. A second loop comprising steps 1054, 1058, 1062, 1066, 1070, 1074, 1080, 1084 and 1088 is executed multiple times until all of the programmed image locations on the integrated circuit 210 have been acquired and analyzed.

When all of the programmed image locations have been inspected, control is transferred via path 1092 to activity block 1094 which indicates that the inspection is complete and it is time to unload the integrated circuit specimen.

Proceeding via path 1096 to activity block 1098, the inspection results for the previously inspected board are output in the form of an inspection report. Control then passes via path 1100 back to the beginning of the inspection routine at activity block 1050 and the system is ready to begin inspection of another integrated circuit.

COMPENSATION FOR ELECTRON BEAM DRIFT

In any electron beam focusing system, thermal effects, high voltage stability, the stability of the electron lens power supplies, the stability of the magnetic lens and deflection power supplies, stray magnetic fields and mechanical instabilities may contribute to a drift in the location of the electron beam 405. Typically, the electron beam drift is on the order of approximately 80 angstroms per minute, and is expected to be caused primarily by the instabilities in the deflection coils 480. An electron beam drift of 80 angstroms per minute is approximately the minimum drift that is achievable using current technology. This electron drift could cause a reduction in the system resolution because a drift in the electron beam 405 typically causes a corresponding drift in the position of the X-ray source, so that the imaged region of the focal plane may be slightly shifted on the detector.

An electron beam drift calibration procedure is periodically employed during the process of acquiring laminographic images in accordance with the present invention. While a laminographic image is being generated, tests are performed at regular intervals to determine if a specified amount of time has elapsed since the last electron beam drift calibration. When the specified time has elapsed, the camera 300 is switched off so that it does not collect further laminographic images. The scan pattern traced by the electron beam on the target is then switched from the circular pattern, generally used to generate laminographic images, to a raster scan pattern. The electron beam is deflected to a selected region, where a fiducial dot is embossed onto the target, so that the region that contains the dot is illuminated by the raster scan pattern. Electrons which are backscattered from the illuminated region are detected by a channeltron, which forms a scanning electron microscope (SEM) micrograph image of the illuminated region. A computer analysis is performed on the SEM micrograph image to determine the distance and direction that the image of the fiducial dot is displaced from the center (or any fixed point) of the image of the illuminated region. Voltage signals appropriate to re-center the dot image within the image of the illuminated (i.e., raster scanned) image are then transmitted to the X and Y deflection coils. This process is repeated for three other dots at other regions on the target. The values of the voltage signals used to recenter the dot images within each of the four illuminated regions are then used to calculate compensation signals which recalibrate the position of the electron beam.

In order to compensate for the electron beam drift, the present invention employs a beam positioning calibration system (shown in FIG. 5) comprising the channeltron 284, the master computer 350, and the image analysis computer 360. The channeltron 284 is advantageously used to create an SEM micrograph image of a region of the target 272 upon which the electron beam 405 is incident. Note that other SEM detectors and devices which image backscattered electrons, X-rays, etc. may be used in lieu of the channeltron 284. This imaging is done using conventional electron microscopy techniques: That is, the area to be imaged is scanned by the electron beam in a predetermined pattern, e.g., a raster scan, and electrons that are backscattered from the surface of the target 272 strike an electron imager within the channeltron 284. Thus, an SEM micrograph image of the scanned region of the surface of the target 272 is generated. The image formed by the backscattered electrons is converted into digital signals which are substantially identical to video signals output by a conventional video camera. The electron micrograph images are then sent to a computer for analysis.

In the present invention, a calibration pattern is advantageously etched onto the target 272. This calibration pattern includes known features that can be easily distinguished in the image produced by the channeltron 284. At selected intervals between normal laminographic imaging, the electron beam 405 is diverted to the calibration area on the target 272, and an SEM micrograph image is formed by electrons which are backscattered from the surface of the target 272 as the electron beam 405 is swept over the calibration area (e.g., using a conventional raster scan). The backscattered electron image of the calibration area of the target 272 allows for analysis of the features on the target 272. If the target 272 were absolutely smooth, then the SEM micrograph image formed by the channeltron 284 would be basically featureless. If a specific pattern were etched or embossed onto the target 272, then the backscattered electron image would reflect these features as changes of electron density. The changes of electron density would correspond to different gray levels in digital memory than would the smooth portions of the target 272.

If the position of the electron beam 405 has drifted since the last calibration sweep, the image of the calibration pattern formed by the backscattered electrons will be shifted from its original calibrated position by a measurable distance. The SEM micrograph image is a video image which is sent to the master computer 350 via line 355. The video image corresponds to a digital image which can be stored in the memory of the master computer 350. The stored digital image is then transferred to the image analysis computer 360.

Once the image is acquired by the image analysis computer 360, an analysis is performed to determine how far the SEM image of the calibration pattern has shifted from its original calibrated position. Voltage offsets appropriate to shift the electron beam 405 back to its original calibrated position are then calculated. The calculated offset voltages are then applied to the deflection coils 480, to recalibrate the electron beam 405, and thereby compensate for the electron beam drift. In one embodiment, it is desired to keep the distance of the electron drift below one-fourth of the spot size (500 angstroms in one embodiment). Since it is expected that the electron beam drift will be on the order of 80 angstroms per minute, and it is desired to control the drift within about 125 angstroms, the calibration procedure is performed approximately once every 85 seconds.

Figure 17:
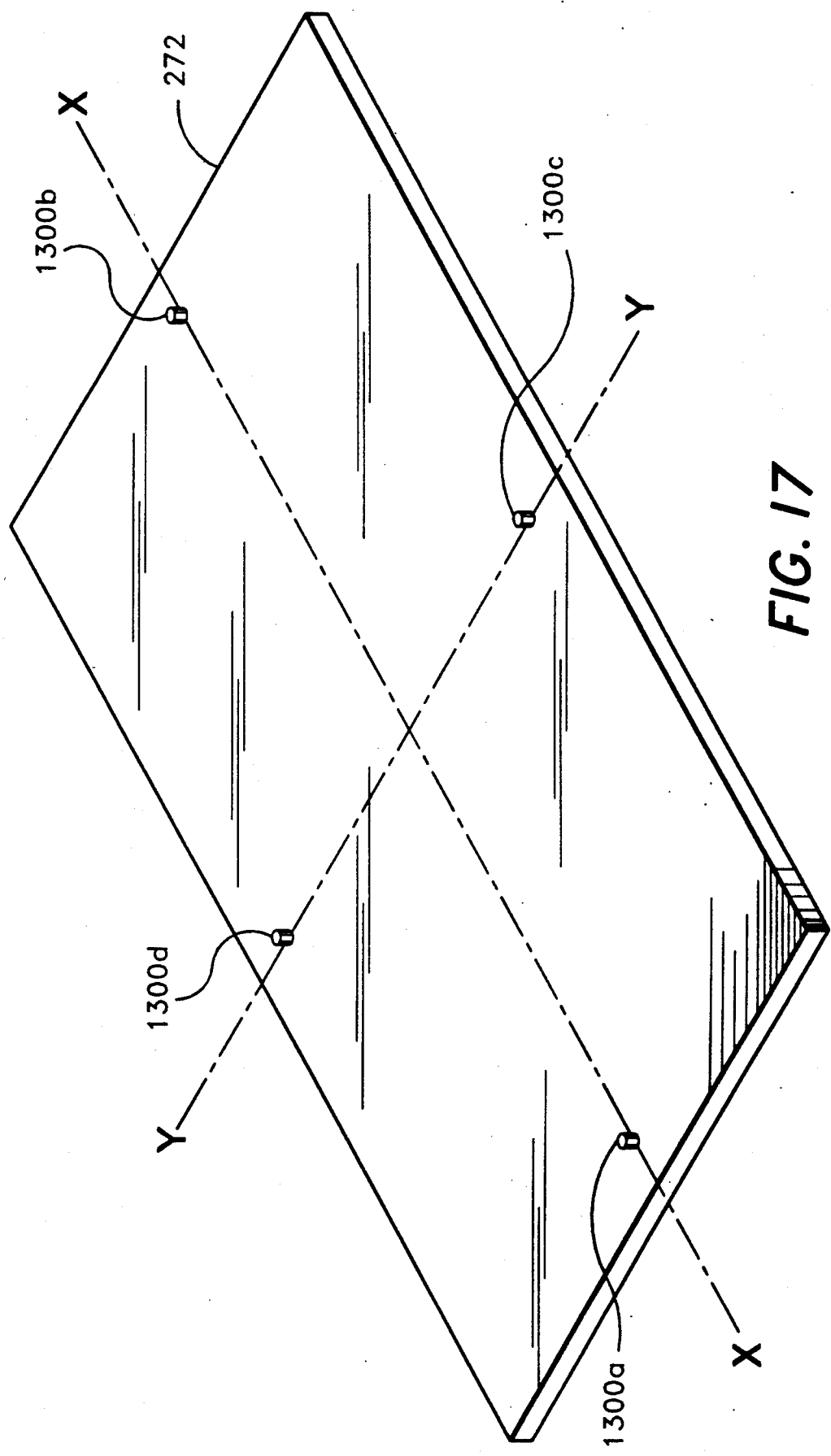
FIG. 17 depicts a possible calibration pattern which may be embossed onto the target.

FIG. 17 depicts one possible calibration pattern which may be formed (e.g., embossed) onto the target 272. Four calibration points, or dots, 1300a, 1300b, 1300c, and 1300d are formed on the target 272 so that they lie near the extremes of the X and Y-axes as shown in FIG. 17. The X and Y-axes depicted in FIG. 17 are defined so that they are perpendicular, and they intersect in the center of the target 272. The size of the laminographic target 272 is expected to be on the order of 0.5 inch by 0.5 inch in one embodiment. The points 1300a–1300d will be small cylindrical features having a diameter of approximately 0.3 microns. The exact locations on the target 272 of each point is stored as CAD data in an LUT, or in the image analysis computer 350, relative to an arbitrary X/Y coordinate system.

Figure 18:
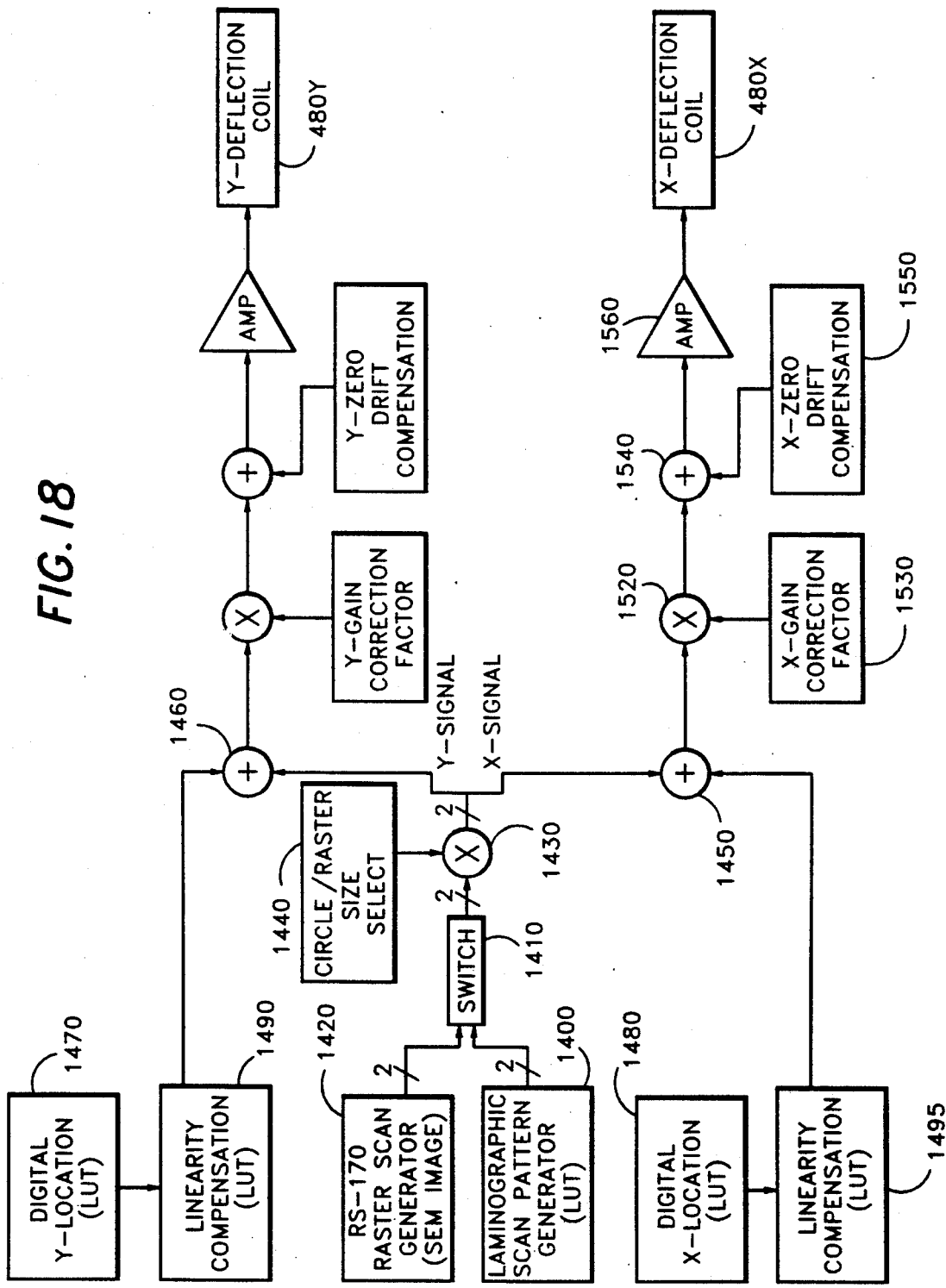
FIG. 18 is a circuit block diagram which shows the basic functions performed by a synchronization Look-Up-Table and drift compensation circuitry used in accordance with the present invention.

A synchronization Look-Up-Table in conjunction with drift compensation circuitry produce control signals which are used to deflect the electron beam and calibrate its position. FIG. 18 is a circuit block diagram which shows the basic functions performed by the synchronization Look-Up-Table and drift compensation circuitry. In one embodiment, the synchronization Look-Up-Table and drift compensation circuitry are implemented within the master computer and the feedback system. It will be understood, however, that the synchronization Look-Up-Table and drift compensation circuitry may also be implemented as external circuitry. A laminographic scan pattern generator 1400 outputs digital approximations to synchronized sine and cosine signals for deflecting the electron beam 405 in an approximately circular scan path on the target 272. The generator 1400 is advantageously implemented as digital signals which are sequentially addressed and output from a digital LUT. The output of the generator 1400 goes to the input of a switch 1410 that switches between the generator 1400 and a raster scan generator 1420. The raster scan generator 1420 is compatible with the video standard RS-170, commonly used in video applications. The output of the switch 1410 goes to a multiplier 1430 which multiplies the signal output from the switch 1410 by a voltage provided by a circle/raster size select 1440. The voltage output by the circle/raster size select 1440 is proportional to the radius of the circular path traced by the X-ray source when the output of the generator 1400 is selected by the switch 1410, or to the dimensions of the region scanned by the raster scan pattern when the output of the raster scan generator 1420. This is because the voltage output from the circle/raster size select 1440 will amplify, via the multiplier 1430, the amplitudes of the horizontal and vertical deflection signals output from the selected generator 1400, or 1420.

The output of the multiplier 1430 is fed to the inputs of an x-adder 1450 and a y-adder 1460. A digital y-location memory 1470 and a digital x-location memory 1480 contain information which indicates coordinate locations designated on the target which correspond to the locations of the regions of the IC device or other object to be imaged. For example, these coordinates could be generated from CAD data which describes the locations of the features of interest on the object.

When the laminography system is initially installed, a test target, which has exactly the same dimensions as the target 272 (FIG. 5), is supported by the table 280 in place of the target 272. The test target advantageously includes a grid pattern which serves to define a coordinate system on the target. The grid pattern comprises a plurality of cross-hairs, or fiducial marks, each of which designates a coordinate on the target. When the electron beam 405 is deflected in a raster scan pattern, an SEM micrograph of selected regions on the surface of the test target (i.e., those regions illuminated by the raster scan) is produced using the channeltron 284. Thus, the cross-hairs which correspond to the coordinates on the target are imaged. The raster scanned electron beam is deflected to each coordinate on the test target, and the deflection voltages which cause the appropriate cross-hairs, or fiducial marks, to be centered within the image are stored within linearity compensation LUT's 1490, 1495. The test target is then replaced by the target 272. Thus, when it is desired to deflect the electron beam 405 to a designated coordinate on the surface of the target 272, that coordinate is accessed via the x- and y-location memories 1480, 1470. The x- and y-location memories 1480, 1470 transmit address signals to the linearity compensation circuitry 1495, 1490, which in turn provide DC offset voltages which cause the electron beam 405 to deflect a desired distance on the target 272 in the x and y directions respectively. In one embodiment, the x- and y-location memories 1480, 1470, as well as the linearity compensation circuitry 1490, 1495 are implemented within a digital LUT. The outputs of the linearity compensation circuit 1490 are input to the y-adder 1460 to obtain a corrected y deflection voltage. Similarly, the outputs of the linearity compensation circuit 1495 are input to the x-adder 1450 to obtain a corrected x deflection voltage. This results in an offset shift for the centroid of the scan pattern produced by the output signal of the multiplier 1430.

The output of the adder 1450 is fed to a multiplier 1520 where it is multiplied by a voltage signal output from an x-gain correction factor generator 1530. For purposes of this discussion, the circuitry used to modify the y deflected signal output from the adder 1460 is substantially identical to the circuitry used to modify the x deflected signal output from the adder 1450. For this reason, the following description will be in reference to the x deflection circuitry only, although it will be understood that the following description will apply to the y deflection circuitry as well. The output of the multiplier 1520 is fed to the input of an adder 1540. A voltage signal which compensates for the electron beam drift in the x direction is also input to the adder 1540 from an x zero drift compensation generator 1550. The compensated signal output from the adder 1540 is then output to an amplifier 1560 which amplifies the signal and transmits it to the X-deflection coil 480X. Similarly, a compensated y deflection signal is transmitted to the Y-deflection coil 480Y.

Figure 19A:
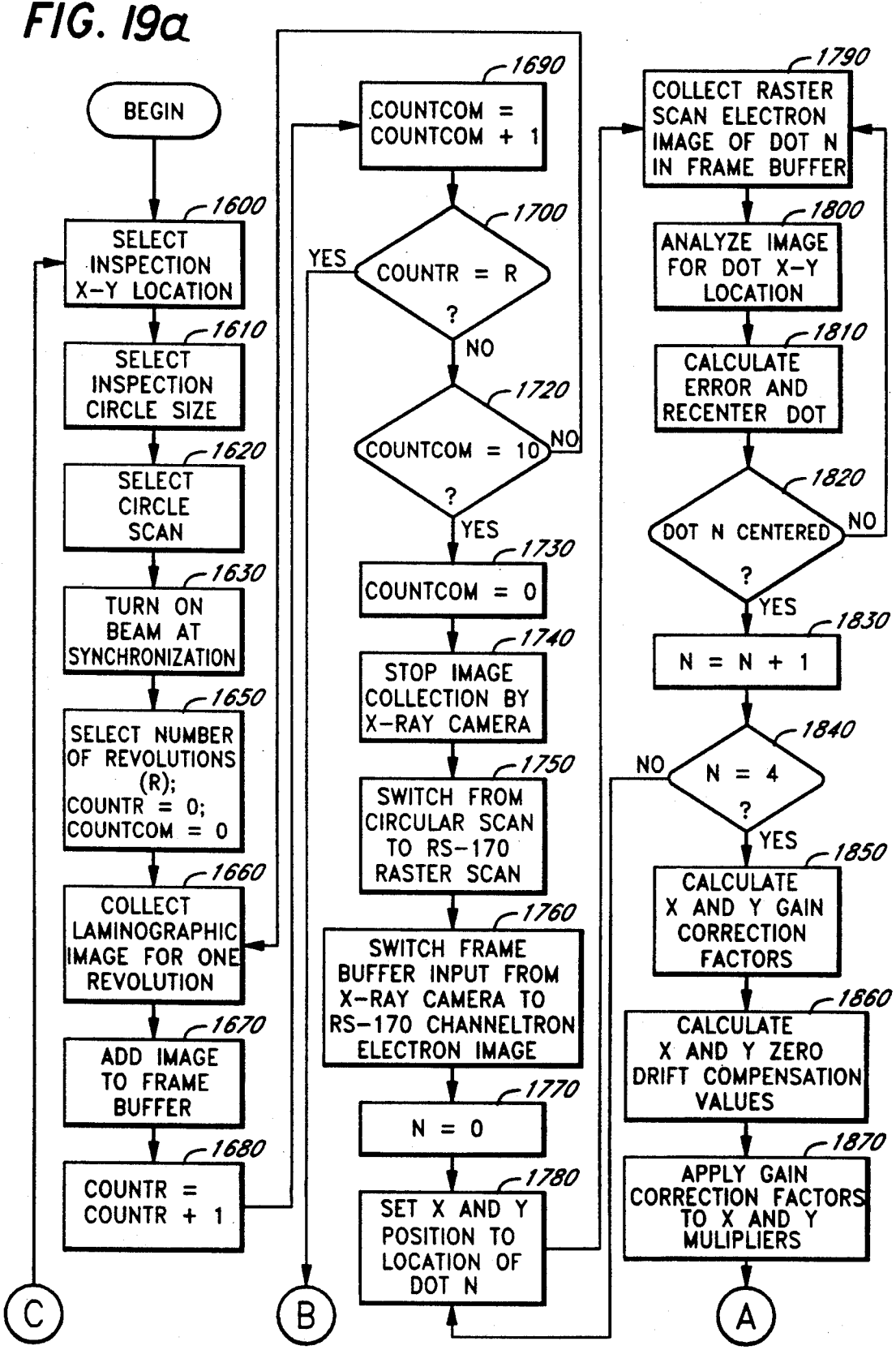
FIGS. 19a and 19b depict a flowchart which details the overall method of obtaining a high resolution laminographic image employed in accordance with the present invention.
Figure 19B:
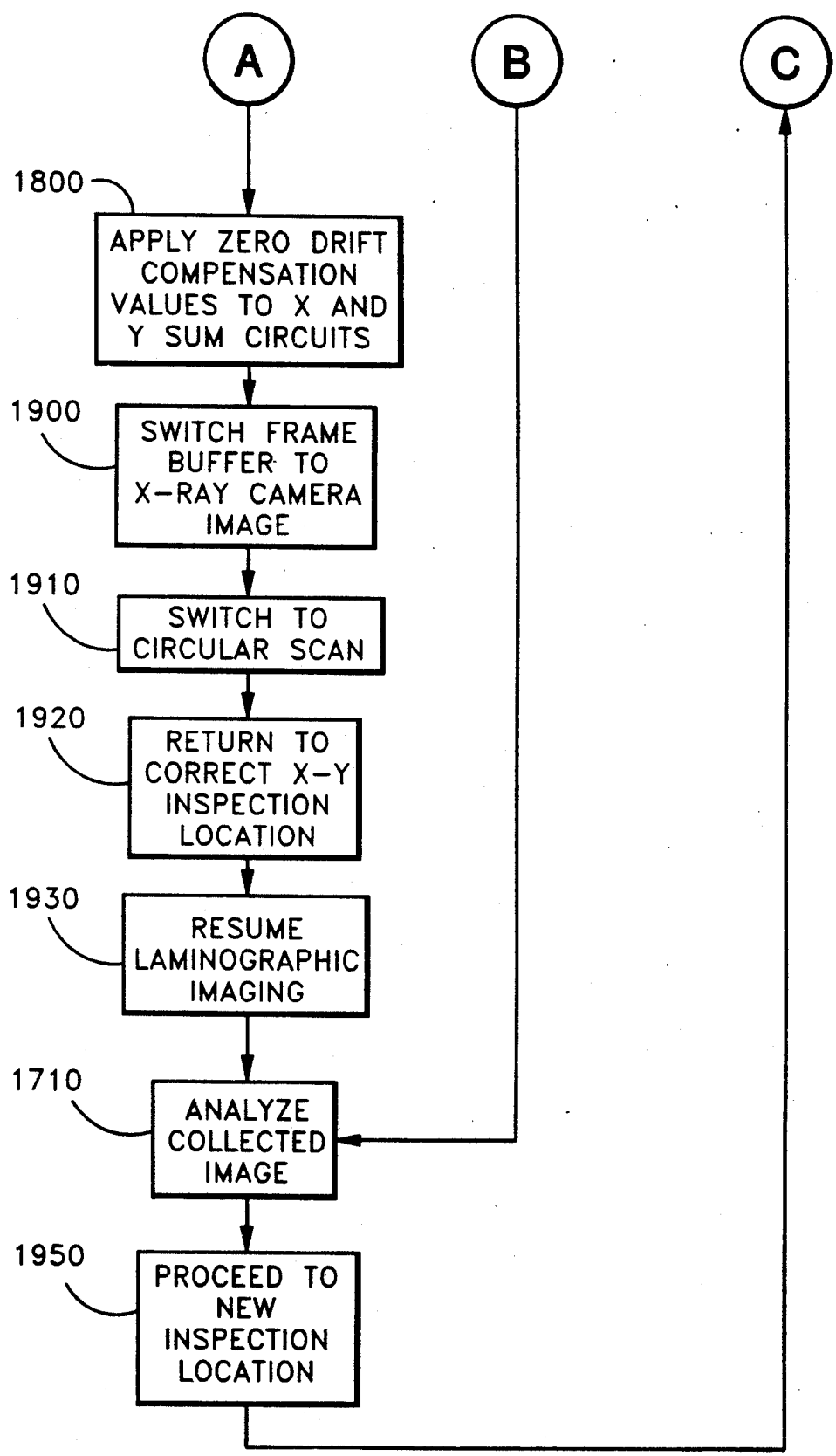

Referring to FIGS. 5, 18, 19a and 19b, the overall method used to produce high resolution laminographs in accordance with the present invention is described. FIGS. 19a and 19b depict a flowchart which details the overall method of obtaining a high resolution laminographic image employed in accordance with the present invention. Initially, the method for obtaining a high resolution laminographic image begins in an activity block 1600 wherein the x and y coordinates of a location to be inspected are selected. This is advantageously done by addressing the appropriate memory locations within the digital X and Y location memories 1480, 1470. The X-Y coordinates of the selected location advantageously correspond to the center of the circular path traced by the X-ray spot on the target 272. Control then passes to an activity block 1610, wherein the size of the circle traced by the X-ray source on the target 272 is selected. As previously mentioned, the size of the trace circle is related to the position along the z axis that the laminographic slice is taken, so that the selection of the trace circle size determines the z axis location of the imaged focal plane. The size of the trace circle is adjusted via the circle/raster size select generator 1440 and the multiplier 1430. Thus, the x, y, and z coordinates of the inspection location are specified within the blocks 1600 and 1610.

Once the x, y, and z coordinates of the inspection location are specified, control passes to an activity block 1620, wherein the output signal produced by the generator 1400 is selected so that the voltages applied to the x and y deflection coils 480 are appropriate to cause the electron beam 405 to be deflected along a circular trace path on the target 272. The output of the generator 1400 is selected via the switch 1410. Control then passes to an activity block 1630, wherein the blanking plates 460 are disabled in response to a synchronization signal, so that the electron beam 405 is allowed to strike the target 272. Prior to the synchronization signal, the electron beam 405 is blanked using the blanking plates and aperture 460, 470 so that it does not strike the target 272. This helps to increase the longevity of the target 272 while maintaining a stable electron beam.

Once the beam 405 has been initiated, control passes to an activity block 1650, wherein the number of complete revolutions of the X-ray source and the detector mirror 290 is selected. Recall that, in one embodiment, the camera 300 integrates 255 frames over the course of one revolution, and this takes approximately 8.5 seconds. The number of complete revolutions for acquiring an image is typically in the range of 1–100. The selected number of revolutions is assigned to the variable R. Variables COUNTR and COUNTCOM are initialized to zero in the activity block 1650. The variable COUNTR is used to keep track of the number of revolutions that are required to produce a high resolution laminographic image, while the variable COUNTCOM is used to keep track of the time elapsed between each electron drift calibration. Control then passes to an activity block 1660, wherein a laminographic image is collected for a single revolution (e.g., 255 frames). This may be done using an image Matrox board for example. The collected image is then added to the frame buffer within the master computer 350, as shown in an activity block 1670. Control then passes to an activity block 1680, wherein the variable COUNTR is incremented by one, and from there to an activity block 1690, wherein the variable COUNTCOM is also incremented by one.

Control proceeds to a decision block 1700, where a test is performed to determine if the value of COUNTR is equal to the value R. If the value of COUNTR is equal to the value of R, this means that the source and detector have completed the selected number of revolutions for acquiring the image, and control passes to an activity block 1710, wherein the image is analyzed. If the value of COUNTR is not equal to the value of R, this implies that further revolutions should be taken before the image is acquired and analyzed, and control passes to a decision block 1720.

In the decision block 1720, a test is performed to determine if the value of COUNTCOM is equal to 10. If the value of COUNTCOM is equal to 10, this implies that ten revolutions have occurred since the initialization of the variable COUNTCOM to zero. Thus, approximately 85 seconds have elapsed since the last calibration has occurred. Therefore, in order to maintain a drift error of no more than 125 angstroms (one-fourth a spot size of 500 angstroms), the calibration procedure is performed after every ten revolutions. If the value of COUNTCOM is equal to 10, then control passes to an activity block 1730. If the value of COUNTCOM is less than 10, then control returns to the activity block 1660, wherein another laminographic revolution is initiated.

Once ten revolutions have been completed, the electron beam drift calibration procedure is initialized. In the activity block 1730, the value of COUNTCOM is reset to zero. Control then passes to an activity block 1740, wherein the camera 300 is prevented from collecting further images (e.g., by closing a camera shutter). Control then proceeds to an activity block 1750, wherein the signal output by the RS-170 raster scan generator 1420 is selected. This is advantageously done via the switch 1410 (FIG. 18). An activity block 1760 is then entered, wherein the input to the frame grabber 1002 of the master computer 350 is switched from the camera 300 to the channeltron 284. This means that the master computer 350 receives video signals transmitted from the channeltron 284, rather than the camera 300. A labeling variable, N, is then initialized to zero in an activity block 1770. Control then passes to an activity block 1780, wherein the electron beam 405 is deflected so that the region of the target 272 which is being raster scanned is centered at the theoretical position of the Nth dot (i.e., dot 1300a, 1300b, 1300c, or 1300d). Control then passes to an activity block 1790, wherein an image formed by the electrons backscattered from the raster scanning on the surface of the target 272 is obtained by the channeltron 284 and transmitted to the frame grabber 1002. The image collected by the frame grabber 1002 is then analyzed to determine the exact X-Y coordinate location of the dot in an activity block 1800. The differential error, in both the x and y directions, between the theoretical position of the Nth dot, and the actual location of the Nth dot as determined by the image analysis, is then calculated within an activity block 1810. The differential error value is advantageously stored as a deflection correcting voltage within a digital LUT. Control then passes to a decision block 1820 to determine if the dot is centered within the image after applying the x and y differential error correction values to the X and Y deflection coils 480X, 480Y. If the dot is not centered after applying the differential error correction values, control returns to the activity block 1790, wherein another image of the Nth dot is collected. The new image is then analyzed, and a new error value is calculated. This procedure continues until the Nth dot is centered. Control then passes to an activity block 1830, wherein the value of N is incremented by one. This indicates that a new dot is to be analyzed and centered. Control passes from the activity block 1830 to a decision block 1840, wherein a test is performed to determine if the value of N is equal to 4. If the value of N is not equal to 4, this implies that differential error values have not been calculated for all four dots (i.e., dots 1300a, 1300b, 1300c, and 1300d). Thus, control returns to the activity block 1780. If the value of N is equal to 4, this implies that differential error values have been calculated for all four dots, and control then passes to an activity block 1850.

In the activity block 1850, the X and Y gain correction factors are calculated. Recall, as discussed in reference to FIG. 18, that the X gain correction factor is multiplied by the x-deflection signal via the multiplier 1520, and the Y gain correction factor is similarly multiplied by the y-deflection signal. The X gain correction factor may be calculated as the ratio between the standard X gain, given the variable name STANDARD-GAINX, of the x-deflection signal, and the new gain, given the variable name NEWGAINX, that is calculated as a function of the measurements made when centering the dot in the channeltron image. Namely, the value of NEWGAINX may be calculated as the difference between a correction voltage designated as DOTX1VOLTS and a correction voltage designated as DOTX2VOLTS, divided by the difference between a correction displacement DOTX1LOCATION and a correction displacement DOTX2LOCATION. That is:

$$NEWGAINX = \frac{(DOTX1VOLTS - DOTX2VOLTS)}{(DOTX1LOCATION - DOTX2LOCATION)}$$

The variables DOTX1VOLTS and DOTX2VOLTS represent the total deflection voltage applied to the X deflection coil 480X when centering the images of the dots 1300a and 1300b respectively. The variables DOTX1LOCATION and DOTX2LOCATION represent the physical distances in the x direction that the dots 1300a and 1300b are initially displaced from the coordinate on the target 272 which corresponds to a deflection voltage of zero volts. The values of DOTX1LOCATION and DOTX2LOCATION may be calculated by counting the number of pixels between the pixel at the center of the image of the dot (1300a for DOTX1LOCATION or 1300b for DOTX2LOCATION) and the pixel corresponding to the zero-volt coordinate. The number of pixels between the center of the analyzed dot image and the zero-volt coordinate pixel can then be multiplied by a distance corresponding to the width of one pixel to obtain the values of DOTX1LOCATION and DOTX2LOCATION.

To obtain the Y gain correction factor, a similar procedure is used. The Y gain correction factor is determined using the physical displacement in the y direction of the zero-volt coordinate from the center of the images of the dots 1300c and 1300d, rather than the dots 1300a and 1300b used to determine the X gain correction factor. Also, the Y gain correction factor is calculated using the total deflection voltages applied to the Y deflection coil 480Y, rather than using the total deflection voltages applied to the X deflection coil 480X. Otherwise, the procedure used to determine the Y gain correction factor is substantially the same as the procedure used to determine the X gain correction factor.

Once the X and Y gain correction factors are calculated in the activity block 1850, control passes to an activity block 1860, wherein the X and Y zero drift compensation values are calculated. Recall that, as discussed in reference to FIG. 18, the X zero drift compensation value is added to the x-deflection signal via the adder 1540, and the Y zero drift compensation value is similarly added to the y-deflection signal. The X zero drift compensation value is calculated as the average of the total x deflection voltages applied to the X deflection coil 480X when centering the dots 1300a and 1300b, minus a voltage, OLDXVOLTS, which is the voltage previously used to deflect the electron beam to the designated location during generation of the linearity compensation LUT's 1490, 1495. This is simply calculated as [(DOTX1VOLTS+DOTX2VOLTS)/2]-OLDXVOLTS. The Y zero drift compensation value is calculated in a similar fashion using the error compensation voltages applied to the Y deflection coil 480Y when centering the dots 1300c and 1300d. Control then passes to an activity block 1870, wherein voltages corresponding to the calculated gain correction factors are generated and applied to the x and y deflection signals via the multiplier circuitry 1520. Control then passes to an activity block 1880, wherein voltages corresponding to the zero drift compensation values are added to the x and y deflection signals via the summing circuitry 1540. Thus, the electron beam drift will be compensated for by means of the X and Y gain correction deflection voltages, and the X and Y zero drift compensation deflection voltages.

Once the electron drift calibration procedure is finished, the laminography system 200 returns to its normal image acquisition routine. Thus, control next passes to an activity block 1900 wherein the frame grabber 1002 within the master computer 350 is switched to once again receive inputs from the camera 300 rather than the channeltron 284. The scan pattern traced by the electron beam 405 is then restored to a circular path within an activity block 1910 by switching to the sine-/cosine generator 1400 via the switch 1410. Control then proceeds to an activity block 1920, wherein the correct X-Y-Z inspection location is returned to (e.g., the location where the laminographic image was being taken prior to the initiation of the electron beam drift calibration procedure). Laminographic imaging is then resumed, as indicated within an activity block 1930. Once the full number of revolutions has been completed for the laminographic image to be acquired, control passes to the activity block 1710, wherein the acquired image is analyzed. Control then passes to an activity block 1950 wherein the electron beam 405 is deflected to begin inspection at a new location. Control then returns to the activity block 1600, and the entire inspection routine is repeated for a desired number of inspection locations.

It should be noted that shifting the position of the path traced by the X-ray source results in a change in the distance of the path followed by the electron beam 405. That is, the distance from the cathode filament 410 to the target surface changes each time a shift is effected in the position of the X-ray source. This results in a change in the focal length of the electron beam 405, so that dynamic focusing of the beam 405 must be brought about in order to keep the focal point of the electrons within the beam 405 at the surface of the target 272. Thus, the present invention advantageously effects a change in voltage applied to the focusing electrodes 490 that is appropriate to maintain the focal point of the beam 405 at the surface of the target 272.

In addition to providing for drift compensation, the ability of the present laminography system 200 to image the target 272, as in an electron microscope, will allow the monitoring of the condition of the target 272 throughout its lifetime.

The apparatus of the present invention is advantageously used to inspect selected regions of integrated circuits for purposes of failure analysis. Thus, the total time required to inspect an entire integrated circuit 210, utilizing the above described routine, is determined by the number of regions which must be analyzed. Depending upon the characteristics to be analyzed, the magnification, and thereby the size of the region corresponding to the field of view, can be varied. For example, if it is desired to inspect the features within a single electrical interconnection 214, then the region corresponding to the field of view may be on the order of 1 mil×1 mil. With a field of view of this size, the pixel resolution will be about 0.002 mils, or 0.058 microns. However, if the feature to be inspected is the overall pattern of multiple trace paths, then the region corresponding to the field of view may have dimensions on the order of 50 mils×50 mils.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A high resolution laminography system comprising:
    a source of X-rays wherein said source of X-rays further comprises:
        a source of electrons which generates an electron beam;
        a deflector for steering said electron beam;
        a target wherein X-rays are emitted from said target when said electron beam impinges upon said target, said target further comprising an imagable feature;
    an SEM detector for producing an SEM micrograph of said target imagable feature in response to illumination of said feature by said electron beam;
    an image analysis system for analyzing characteristics of said SEM micrograph image of said target imagable feature, and providing an output signal in response to said analysis; and
    a feedback system which receives said output signal from said image analysis system, processes said output signal and provides a control signal to said electron beam deflector; and
    a laminographic detector for producing a cross sectional image of a cutting plane of an object illuminated by said X-rays emitted by said target.

2. A system as defined in claim 1, wherein said feedback system comprises a digital Look-Up-Table.

3. A system as defined in claim 1, wherein said imagable feature on said target comprises four points, wherein two of said points lie on a line which is perpendicular to a line defined by two others of said points.

4. A system as defined in claim 1, wherein said target comprises a plurality of concentric rings.

5. A system as defined in claim 1, wherein said target has a cylindrical interior surface.

6. A system as defined in claim 1, wherein said SEM detector comprises a channeltron imager.

7. A system as defined in claim 1, further comprising an electron collector for preventing electrons from striking said object.

8. A system as defined in claim 1, further including a piezoelectric translation stage for vertically positioning said object.

9. A system as defined in claim 1, wherein said detector comprises a fluorescent screen, an optical derotation device and a camera.

10. A system as defined in claim 9, wherein aid fluorescent screen comprises Gadolinium Oxysulfide.

11. A method of producing high resolution laminographs, comprising the steps of:
    producing a source of X-rays, wherein said step of producing X-rays further comprises the steps of:
        generating an electron beam;
        steering said electron beam with a deflector;
        striking a target with said electron beam, wherein X-rays are emitted from said target when said electron beam impinges upon said target, said target having an imagable feature;
    producing an SEM micrograph of said target imagable feature in response to illumination of said feature by said electron beam;
    analyzing characteristics of said SEM micrograph image of said feature, and providing an output signal in response to said analysis; and
    providing a feedback system which receives said output signal from said image analysis system, processes said output signal and provides a control signal to said electron beam deflector; and
    producing a cross sectional image of a cutting plane of an object illuminated by said X-rays using a laminographic detector.

12. A method as defined in claim 11, wherein said analyzing step comprises the steps of:

determining the location of said feature image within said micrograph;

calculating the distance between the determined location of said feature image and the center of said micrograph; and producing a voltage signal as a function of said calculated distance appropriate to cause said feature image to be centered within said micrograph.

13. A high resolution laminography system comprising:

- a source of X-rays wherein said source of X-rays further comprises:
  - a source of electrons which generates an electron beam;
  - a deflector for steering said electron beam;
  - a target wherein X-rays are emitted from said target when said electron beam impinges upon said target, said target further comprising a target imagable feature;
- a first detector for producing an image of said target imagable feature;
- an image analysis system for analyzing characteristics of said image of said target imagable feature, and providing an output signal in response to said analysis; and
- a feedback system which receives said output signal from said image analysis system, processes said output signal and provides a control signal to said electron beam deflector; and
- a laminographic detector for producing a cross sectional image of a cutting plane of an object illuminated by said X-rays emitted by said target.

14. A system as defined in claim 13, wherein said first detector further comprises an SEM detector and produces a micrograph of said target imagable feature.

* * * * *